US007373207B2

(12) United States Patent
Lattouf

(10) Patent No.: US 7,373,207 B2
(45) Date of Patent: May 13, 2008

(54) TREATMENTS FOR A PATIENT WITH CONGESTIVE HEART FAILURE

(76) Inventor: Omar M. Lattouf, 4262 Regency Ct. NW., Atlanta, GA (US) 30327

( * ) Notice: Subject to any disclaimer, the term of this patent is extended or adjusted under 35 U.S.C. 154(b) by 403 days.

(21) Appl. No.: 10/313,198

(22) Filed: Dec. 6, 2002

(65) Prior Publication Data
US 2003/0120264 A1 Jun. 26, 2003

Related U.S. Application Data

(63) Continuation-in-part of application No. 10/295,390, filed on Nov. 15, 2002, now Pat. No. 6,978,176.

(60) Provisional application No. 60/369,988, filed on Apr. 4, 2002, provisional application No. 60/365,918, filed on Mar. 20, 2002, provisional application No. 60/340,062, filed on Dec. 8, 2001.

(51) Int. Cl.
A61N 1/372 (2006.01)
(52) U.S. Cl. .............................. 607/130; 607/3; 607/4; 607/5; 607/9; 607/10; 607/129; 607/131; 600/16; 600/17
(58) Field of Classification Search ................ 607/3–5, 607/9–10, 129–131; 600/16–17
See application file for complete search history.

(56) References Cited
U.S. PATENT DOCUMENTS

| 3,844,292 | A | 10/1974 | Bolduc |
| 4,207,903 | A | 6/1980 | O'Neill |
| 4,280,510 | A | 7/1981 | O'Neill et al. |

(Continued)

FOREIGN PATENT DOCUMENTS

WO WO 98/07375 2/1998

(Continued)

OTHER PUBLICATIONS

Written Opinion in International Patent Application PCT/US02/39087, mailed Jan. 21, 2005.

(Continued)

Primary Examiner—Carl Layno
Assistant Examiner—Deborah Malamud
(74) Attorney, Agent, or Firm—Edward J. Lynch

(57) ABSTRACT

The invention is directed to devices for two minimally invasive therapeutic procedures, particularly for patients with congestive heart failure. One procedure involves providing a valve to form a passageway through the patient's left ventricular wall at the apex of the patient's heart and configured to advance instruments through the valved passageway to connect the valve leaflets of the patient's heart valve, e.g. the mitral valve, in a "Bow-Tie" configuration to prevent or minimize regurgitation through the valve. The second procedure is directed to a pacing lead with a housing and a pacing lead implanting device which are configured to pass through a trocar in the patient's chest and implanting the pacing lead on an exposed epicardial region of the patient's heart wall. The pacing lead has a penetrating electrode which is secured within the heart wall. One or both procedures may be performed on a patient with CHF. Other improved instruments include a leaflet connector with an artificial cordae tendenae strand secured to an end of the leaflet connector.

9 Claims, 19 Drawing Sheets

U.S. PATENT DOCUMENTS

| | | | |
|---|---|---|---|
| 4,357,946 A | 11/1982 | Dutcher et al. | |
| 4,424,818 A | 1/1984 | Doring et al. | |
| 4,475,560 A | 10/1984 | Tarjan et al. | |
| 4,936,304 A | 6/1990 | Kresh et al. | |
| 5,336,252 A | 8/1994 | Cohen et al. | |
| 5,571,215 A | 11/1996 | Sterman et al. | |
| 5,618,287 A * | 4/1997 | Fogarty et al. | 606/129 |
| 5,665,109 A | 9/1997 | Yoon et al. | |
| 5,716,392 A | 2/1998 | Bourgeois et al. | |
| 5,758,664 A * | 6/1998 | Campbell et al. | 128/898 |
| 5,766,163 A | 6/1998 | Mueller et al. | |
| 5,855,592 A * | 1/1999 | McGee et al. | 607/4 |
| 5,904,711 A * | 5/1999 | Flom et al. | 607/12 |
| 5,964,793 A * | 10/1999 | Rutten et al. | 607/119 |
| 5,978,714 A * | 11/1999 | Zadini et al. | 607/129 |
| 6,010,526 A | 1/2000 | Sandstrom et al. | |
| 6,079,414 A | 6/2000 | Roth | |
| 6,087,394 A * | 7/2000 | Duhaylongsod | 514/478 |
| 6,139,555 A | 10/2000 | Hart et al. | |
| 6,162,195 A | 12/2000 | Igo et al. | |
| 6,224,617 B1 * | 5/2001 | Saadat et al. | 606/170 |
| 6,231,518 B1 | 5/2001 | Grabek et al. | |
| 6,258,069 B1 | 7/2001 | Carpentier et al. | |
| 6,258,105 B1 | 7/2001 | Hart et al. | |
| 6,345,198 B1 * | 2/2002 | Mouchawar et al. | 607/4 |
| 7,146,225 B2 | 12/2006 | Guenst et al. | |
| 7,270,669 B1 | 9/2007 | Sra | |
| 2003/0130571 A1 * | 7/2003 | Lattouf | 600/374 |

FOREIGN PATENT DOCUMENTS

| | | |
|---|---|---|
| WO | WO 99/11201 | 3/1999 |
| WO | WO 99/00059 | 7/1999 |
| WO | WO 00/60995 | 10/2000 |
| WO | WO 01/28432 | 4/2001 |

OTHER PUBLICATIONS

International Search Report for PCT/US02/28101 mailed Apr. 7, 2003.

European Search Report for EP 02 79 9216 mailed Oct. 10, 2006.

* cited by examiner

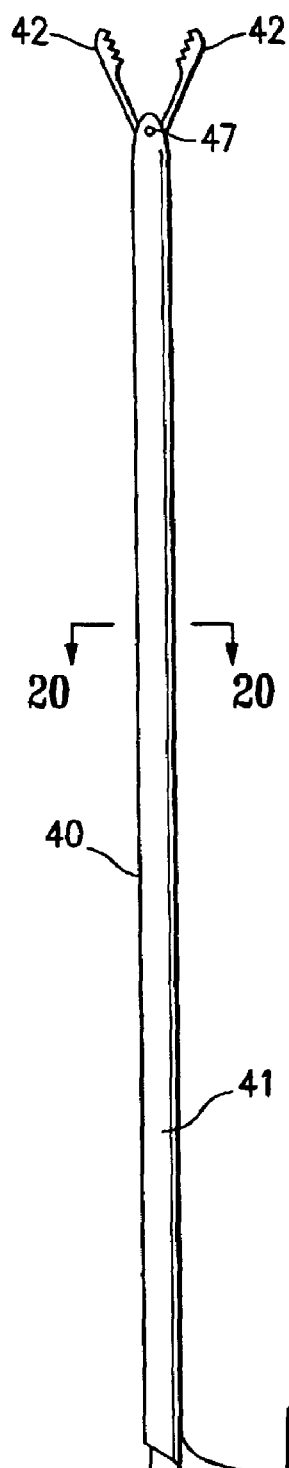
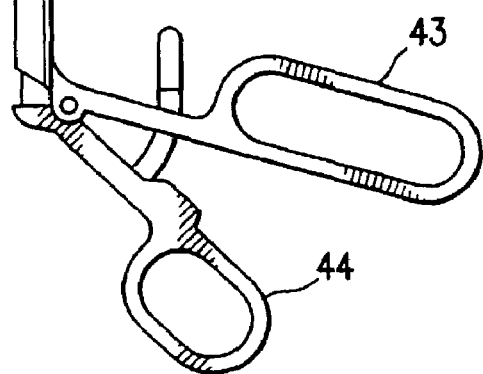
FIG. 19
FIG. 20

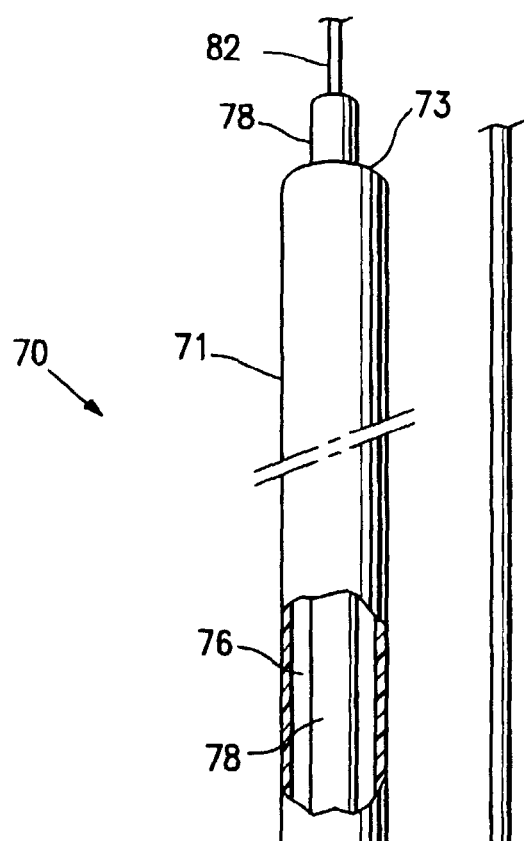
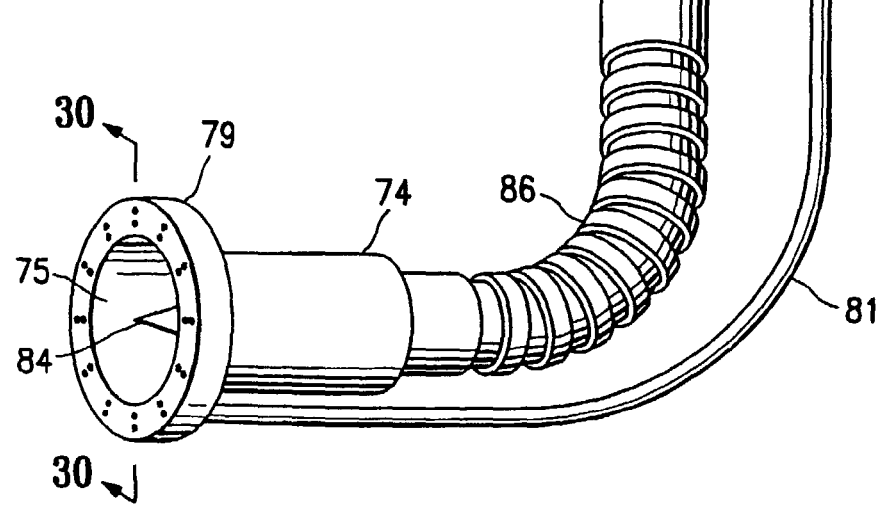
FIG. 29

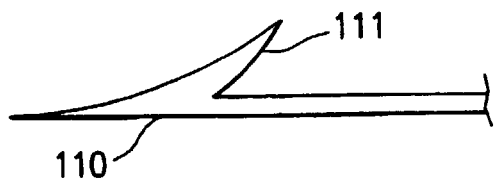
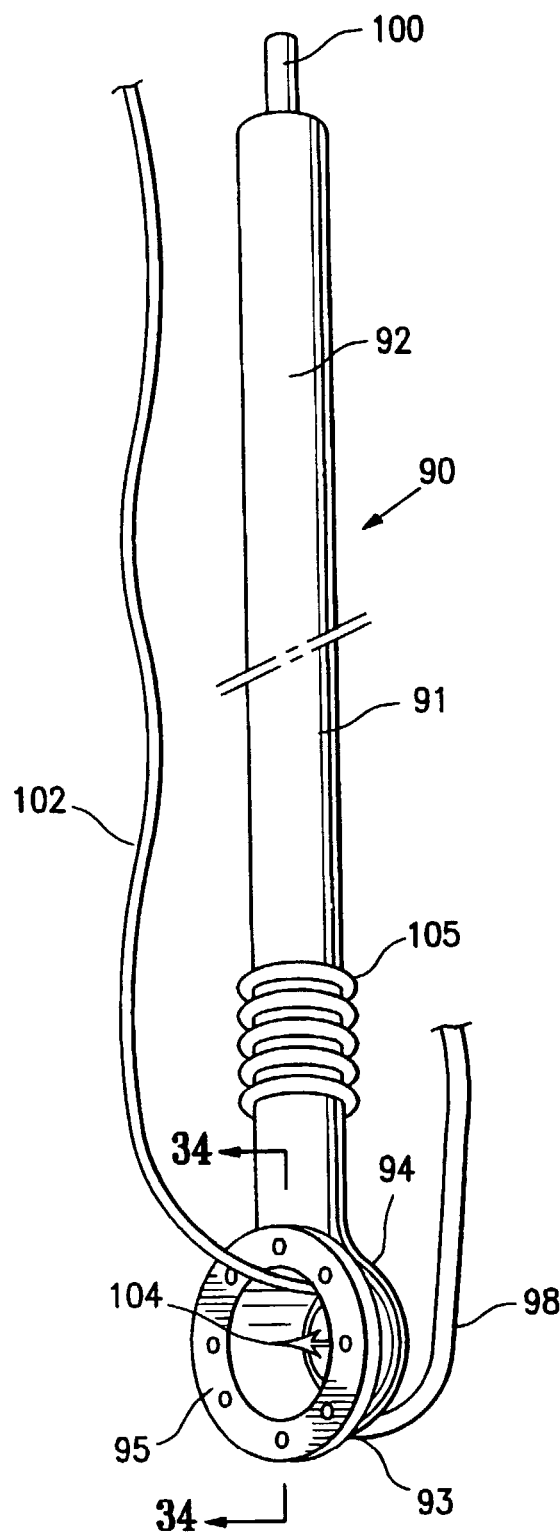
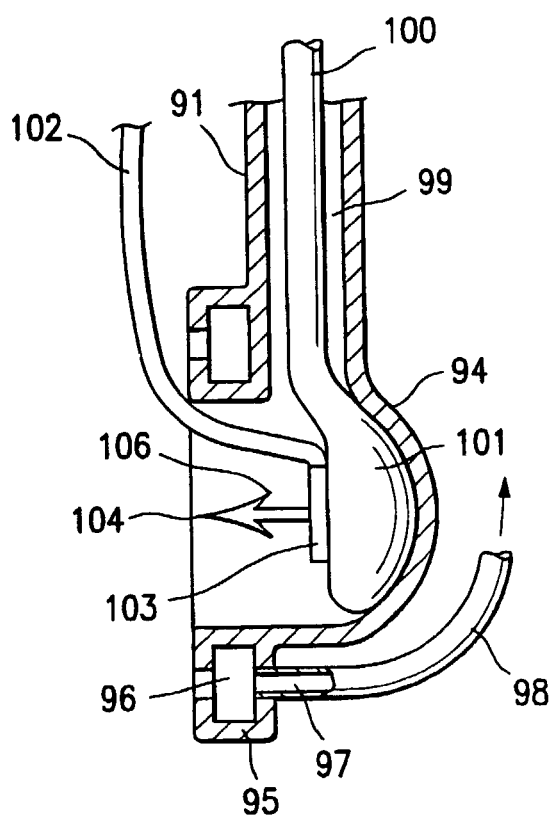

TREATMENTS FOR A PATIENT WITH CONGESTIVE HEART FAILURE

CROSS REFERENCE TO RELATED APPLICATIONS

This application is a continuation-in-part of application Ser. No. 10/295,390, filed on Nov. 15, 2002, now U.S. Pat. No. 6,978,176 which is related to and claims the priority of Provisional Application No. 60/340,062, filed Dec. 8, 2001, Provisional Application Ser. No. 60/365,918, filed Mar. 20, 2002, and Provisional Application Ser. No. 60/369,988, filed Apr. 4, 2002. The entire contents of these applications are incorporated herein by reference.

BACKGROUND OF THE INVENTION

This invention is directed to therapeutic procedures for a patient's heart and to instruments and systems for such procedures. The invention is particularly suitable for treating a patient suffering from the symptoms of congestive heart failure (CHF), and particularly to those CHF patients exhibiting mitral valve regurgitation (MVR) and/or those exhibiting intraventricular conduction delay with resulting disturbance of the synchronous right and/or left ventricular contractility.

There are over five million patients in the United States suffering from CHF and there are more than seven hundred thousand new cases of CHF each year. For many of these patients medical therapy is not very successful. Recent trials have shown that a significant number of CHF patient's benefit from percutaneous ventricular pacing where pacing leads are introduced percutaneously and advanced within the patient's vasculature until the leads are disposed within the patient's coronary sinus. However, ventricular pacing has not been found successful for a significant number of CHF patients for a variety of reasons. For example, in a number of procedures the coronary sinus cannot be cannulate due to dilated cardiomyopathy (the deformity of the heart which accompanies CHF) and, even if the coronary sinus is cannulated, the pacing leads can become displaced rendering them ineffective.

With many CHF patients, their ventricular ejection fraction is reduced due to mitral valve regurgitation (MR) which may also result from dilated cardiomyopathy. The MR in turn can exacerbate the cardiomyopathy leading to a worsening of the MR. The MR can also be the result of torn cordae tendenae which extend from the valve leaflets to the papillary muscles, preventing complete closure of the valve.

Surgical procedures for mitral valve repair for MR typically involves valve support ring at the base of valve. Recent advances in mitral valve repair include securing together the free edges of the mitral valve leaflets by sutures, staples and the like, commonly called "Bow-Tie" or "edge to edge" techniques. These procedures usually involve open heart surgery, including cardiopulmonary bypass and a sternotomy, although more recently suggestions have been made of performing these procedures with minimally invasive and percutaneous techniques which can reduce the morbidity of such procedures. Percutaneous procedures impose difficulties in instrument design because the instruments for such procedures must be long enough to extend from the entry location on the patient's leg to the interior of the patient's heart chamber, and they must have small enough profile and have sufficient flexibility for advancement through the patient's vasculature into the patient's heart chamber. Additionally, the instruments for such percutaneous procedures must also be able to accurately locate the operative distal ends of such instruments at a desired location within the chambers of the patient's beating heart and be strong enough to perform the required functions.

Techniques for Bow-Tie repair of mitral valves have been mentioned in the patent literature, but specific instruments for such techniques are not yet commercially available.

SUMMARY OF THE INVENTION

This invention generally relates to minimally invasive therapeutic procedures, including valve repair and ventricular pacing, for patients with CHF and to the devices and systems suitable for use in such procedures. Specifically, one feature of the invention is directed to gaining access to the patient's heart valve, preferably from within the heart chamber. Such acces may be gained through the wall of the patient's heart, such as at the apex thereof, for repairing damaged or otherwise incompetent heart valves. The invention is also directed to the attachment of a pacing lead to an exterior region of the patient's heart wall for ventricular pacing. These procedures provided alone and particularly when performed together provide significant relief and longer life to symptomatic CHF patients. Moreover, due to the minimally invasive nature of these procedures, many of the CHF patient population, who are otherwise unsuitable for conventional surgical treatments, may be treated with the present procedures. As used herein the expression "minimally invasive" refers to procedures in which one or more small openings are made in a patient's chest wall to insert the instruments to be used in performing or observing the procedure. Typically, such procedures utilize trocars within the small chest wall openings having inner lumens with transverse dimensions not greater than 20 mm, preferably about 5 to about 15 mm.

The procedure related to valve repair generally includes first gaining access to the patient's chest cavity through a small opening made in the patient's chest, preferably though an intercostal space between two of the patient's ribs. Such accessing can be effected thorocoscopically through an intercostal space between the patient's ribs by minimally invasive procedures wherein a trocar or other suitable device is placed within the small opening made in the patient's chest.

To the extent required, the patient's deflated lung is moved out of the way, and then the pericardium on the patient's heart wall is removed to expose a region of the epicardium. The patient's heart wall is pierced at the exposed epicardial location to provide a passageway through the heart wall to a heart cavity such as the left ventricle, defined in part by the pierced heart wall. Preferably, the passageway is formed through a region of the heart wall at or near the apex of the patient's heart. Suitable piercing elements include a 14 gauge needle. A guide wire is advanced through the inner lumen of the needle into the heart chamber and further advanced through the valve to be treated, e.g. the mitral valve, into an adjacent heart chamber. The penetrating needle may then be removed leaving the guide wire in place. A valve for the ventricular wall is advanced over the guide wire and installed in the ventricular wall passageway formed by the needle. The valve is configured to enable passage of instruments for the procedure through the heart wall into the heart chamber while preventing loss of blood through the passageway. The valve may be disposed permanently or temporarily within the heart wall passageway.

The valve has a cylindrical body with a valve element disposed within an inner lumen of the cylindrical body. At least the distal end and preferably both ends of the valve are provided with securing elements such as hooks or barbs to fix or otherwise secure the valve within the heart wall passageway. An inflatable dog-boned shape balloon may be utilized to seat the securing elements of the valve within the passageway. Suitable other means for securing valve in the ventricular wall include adhesives, sutures, clip and the like. The valve element within the inner lumen of the valve may take a variety of forms, but a duck-billed valve oriented toward the heart chamber is presently preferred.

The instruments for performing the procedure may be passed through the valve seated in the ventricular passageway. The proximal ends of these instruments extend out of the patient to allow the instruments to be manually or robotically manipulated to accurately position the operative ends of the instruments at the desired location within the heart chamber to perform the procedure and to operate the operative member which may be provided on the distal ends of these instruments from outside the patient's body.

For "Bow-Tie" valve repair on a beating heart, the valve leaflets should be stabilized to facilitate grasping the leaflets with a suitable grasping device at a grasping location and then securing the free edges of the valve leaflets together by suitable connecting members such as one or more sutures, clips or staples or adhesive to form the "Bow-Tie" connection. A suitable stabilizing instrument, particularly for mitral or atrioventrical valve repair, is an elongated catheter having one or more expandable members on a distal location thereof, such as an inflatable balloon or expandable arms, which can engage the atrial surface of the valve leaflets to stabilize and urge the valve leaflets toward the grasping location. The grasping member grasps and holds the valve leaflets together so that the free edges of the leaflets can be secured together by suitable connecting member or element. The elongated stabilizing instrument is advanced through the ventricular wall valve, through the heart chamber defined in part by the ventricular wall until the distal extremity of the instrument having the expandable member(s) is advanced through the heart valve into the heart chamber beyond the heart valve, which in this case is the left atrium. The expandable member(s) e.g. an inflatable balloon or one or more arms are expanded and then the stabilizing instrument is pulled proximally so the expandable member(s) engage the atrial side of the valve leaflets and move the valve leaflets into the grasping location within the ventricular chamber, e.g. left ventricle.

An elongated grasping device with at least a pair of grasping members such as jaws on the distal end thereof for grasping tissue structure is advanced through the ventricular wall valve until the distal end of the device extends into the heart chamber. The grasping members or jaws of the grasping device are operated from the proximal end of the grasping device which extends out of the patient's chest. The jaws of the grasping device are opened to receive the stabilized valve leaflets in the grasping location and then closed to grip the leaflets so that the free edges of the valve leaflets are placed into an operative position for the "Bow-Tie" repair. The free edges of the grasped valve leaflets may be joined or otherwise secured together by suitable connecting elements. Once the free edges of the valve leaflets are secured together, the instruments for the procedure may be withdrawn through the ventricular wall valve and then the opening in the patient's chest. The ventricular wall valve will close upon instrument removal to eliminate or at least minimize blood leakage through the valve. The ventricular wall valve may be left in place or the valve may be removed and the passageway sutured or otherwise suitably closed.

When there is cordae tendenae damage with the heart valve, particularly when there is severance of the cordae tendenae from the valve leaflet or the papillary muscle, repair of the valve leaflet, even by means of the "Bow-Tie" technique, may not prevent reshaping of the ventricular architecture which can reduce ventricular output.

In that instance, it has been found that providing an artificial cordae tendenae such as a strand with one end secured to the secured valve leaflets and another end secured to the heart wall, particularly in the same orientation as the natural cordae tendenae, will support the connected valve leaflets in more or less a normal manner to minimize ventricular deformation (e.g. dilated cardiomyopathy) which leads to decreased output. One end of the strand is secured to the connecting element securing the free edges of the valve leaflets or to the connected free edges themselves and the other end of the strand is secured to a location on the heart wall, preferably on the exterior of the heart wall passing through the ventricular wall valve or if the valve is removed through the ventricular wall passageway. The strand should be relatively inelastic or non-compliant to ensure an effective closed position of the leaflets. A suitable strand material is polytetrafluoroethylene (PTFE). In this case it is preferred that the passageway through the ventricular wall pass through the apex region of the heart between the two papillary muscles in the left ventricle, so that the pull on the valve leaflets by the strand secured to the leaflets is in approximately the same angle or orientation as the natural pull by the competent cordae tendenae. This provides for a better seal of the leaflets and thereby minimizes leakage through the valve. The "Bow-Tie" procedure in conjunction with the use of an artificial cordae tendenae extending between the secured valve leaflets and the heart wall may be used with mini-thoracotomy procedures and open chest procedures, both on and off pump, in addition to the minimally invasive procedures described herein.

While the procedure directed to accessing a patient's heart chamber is primarily described herein for repairing damaged or otherwise incompetent valves between chambers of the patient's heart, the procedure and the instruments for such procedures can be employed in a variety of treatments or diagnoses within the patient's heart chambers. Other procedures which may be performed include transmyocardial revascularization (TMR), aortic stenting for aortic dissections and aneurysm therapy, removal or clots and vegetations of prosthetic valves, excision of heart tumors, stem cell and vascular growth factor implantation, ventricular septal defect closure and the like. In TMR procedures a tissue ablation instrument is advanced into the heart chamber to ablate tissue in an ischemic region of the ventricular wall. It is generally thought that the tissue ablation in the ischemic region causes or results in angiogenesis and thus revascularization which returns blood flow to the ischemic region. For TMR procedures in some regions of the heart chamber, a guiding catheter having a preshaped distal tip may be needed to orient the ablating tip to the desired ischemic region of the patient's heart wall. A similar procedure may be utilized to ablate regions of the intraventricular wall to terminate or curtail arrhythmia. Other procedures are contemplated.

The minimally invasive procedure for placement of a pacing lead having a penetrating electrode is performed through a small opening in the patient's chest formed in the intercostal space between the patient's ribs. The small opening is preferably provided with a suitable trocar such as those available commercially. The pericardium is removed from the desired region of the patient's heart to expose the underlying epicardium. The distal end of the pacing lead is introduced into the patient's chest cavity through the trocar seated in the small opening in the patient's chest and the penetrating electrode on the distal end of the pacing lead is inserted into the ventricular wall through the exposed epicardial surface. The proximal end of the pacing lead is configured to be connected to an electrical power source such as those power sources used for pacing purposes. Such power sources produce a pulsed electrical output of suitable frequency, current and voltage levels to control the contraction of the ventricular wall to which the pacing lead is attached. The proximal end of the pacing lead may be tunneled subcutaneously to the power source which is preferably located in the infraclavical pocket. The penetrating electrode preferably has one or more hooks or other suitable structure for preventing or minimizing the chances for removal of the electrode from the heart wall. The penetrating electrode on the distal end of the pacing lead may take the form of an arrow, fish-hook or helical coil. Other shapes are suitable.

The devices suitable for installing the pacing lead in the exterior of the heart wall are configured to be advanced through the trocar or small opening in the patient's chest and to press or otherwise put the penetrating electrode of the pacing lead within the ventricular wall. The device has a vacuum or other suitable system such as releasable hooks or grasping components on the distal end thereof to secure the distal end of the device to the exposed surface of the epicardium in order to facilitate the placement of the penetrating electrode. The pacing lead and the delivery device are operatively connected with a force applying member that applies the force to the distal portion of the pacing lead required for the electrode to penetrate the ventricular wall. Once the electrode is properly secured within the ventricular wall, the electrical pulses emitted from the pacing electrode override the natural pulses to control the contraction of the heart wall.

The blood flow output from the CHF patient's heart due to the pacing and valve repair in accordance with the present invention is greatly increased, and leads to significant improvement in the physical well being, the life extension and the quality of life of the CHF patient.

These and other advantages of the invention will become more apparent from the following detailed description and accompanying exemplary drawings.

BRIEF DESCRIPTION OF THE DRAWINGS

FIG. 19 is an elevational view of a grasping device embodying features of the invention.

FIG. 20 is a transverse cross-sectional view of the grasping device shown in FIG. 19 taken along the lines 20-20.

Figure 26A:
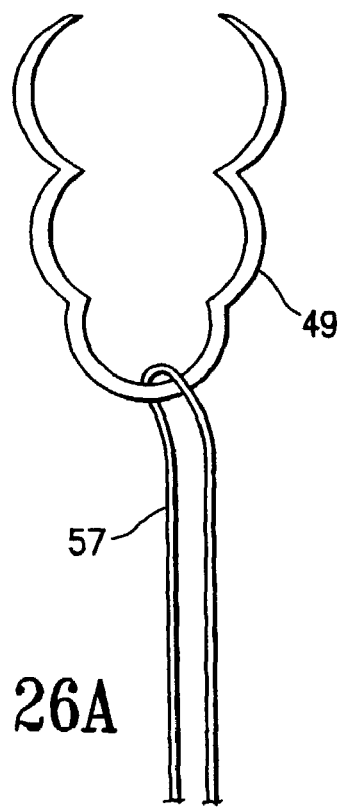
Figure 26B:
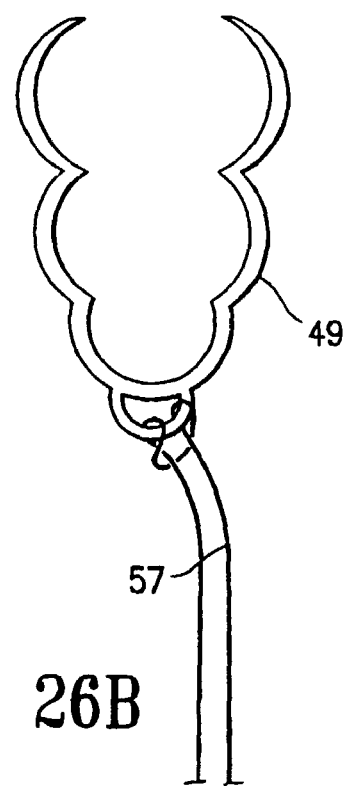

FIG. 26A is an enlarged elevational view of the clip with an artificial cordae tendenae strand secured to the closed end of the clip. FIG. 26B is an alternative clip construction which has an eyelet for securing the end of the artificial cordae tendenae.

Figure 27:
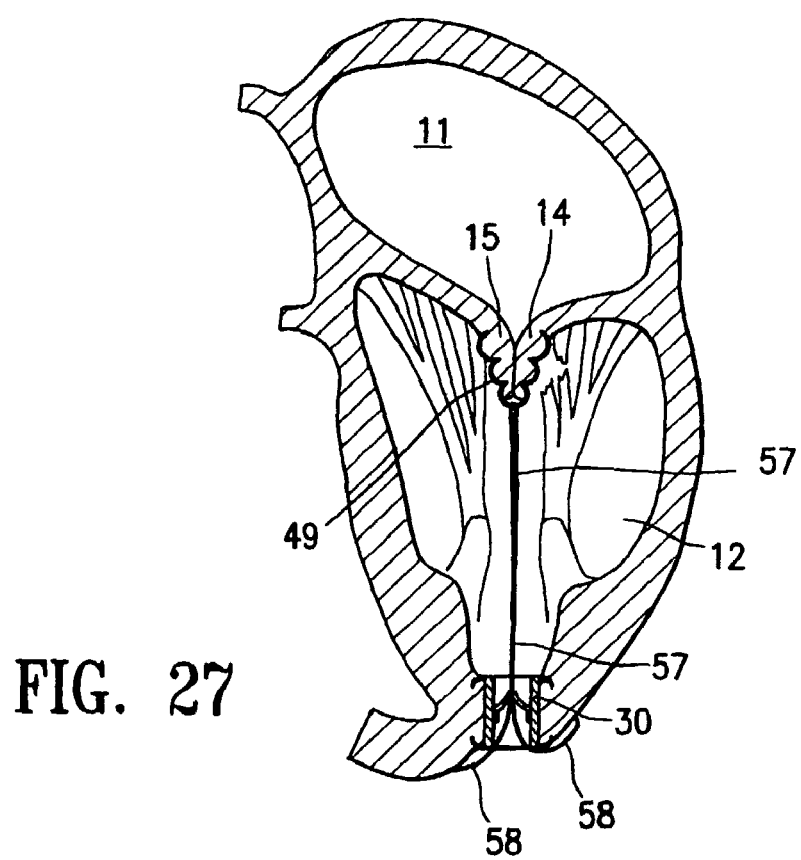

FIG. 27 is a partial elevational view, in section of the left side of a patient's heart illustrating the artificial cordae tendenae extending from the clip to the exterior of the patient's heart.

Figure 28:
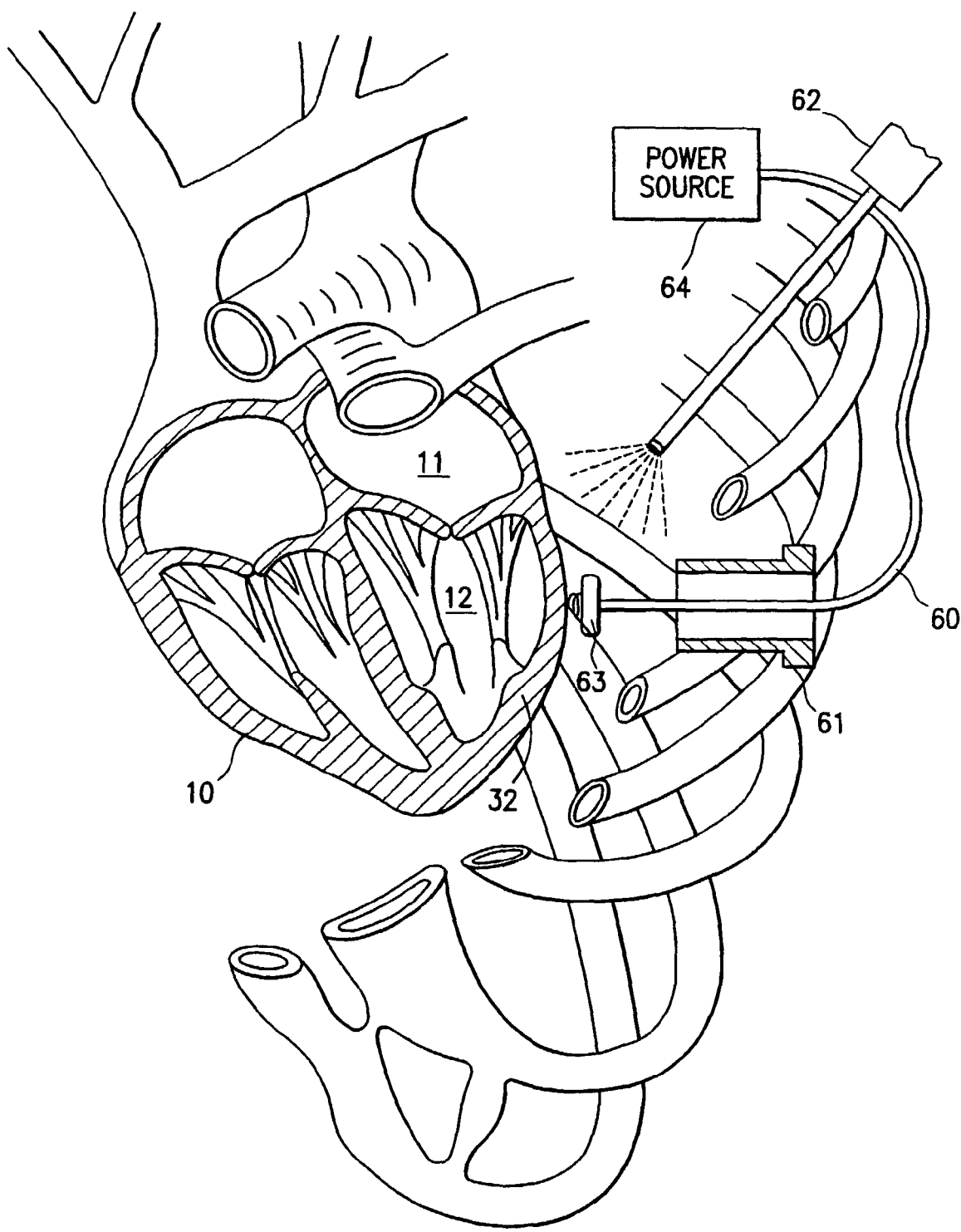

FIG. 28 is a perspective view of a patient's chest, illustrating the location of the patient's heart within the chest cavity, with part of the heart wall removed to expose the left ventricular chamber and illustrating placement of the penetrating electrode of a pacing lead within the heart wall defining in part the left ventricle.

Figure 30:
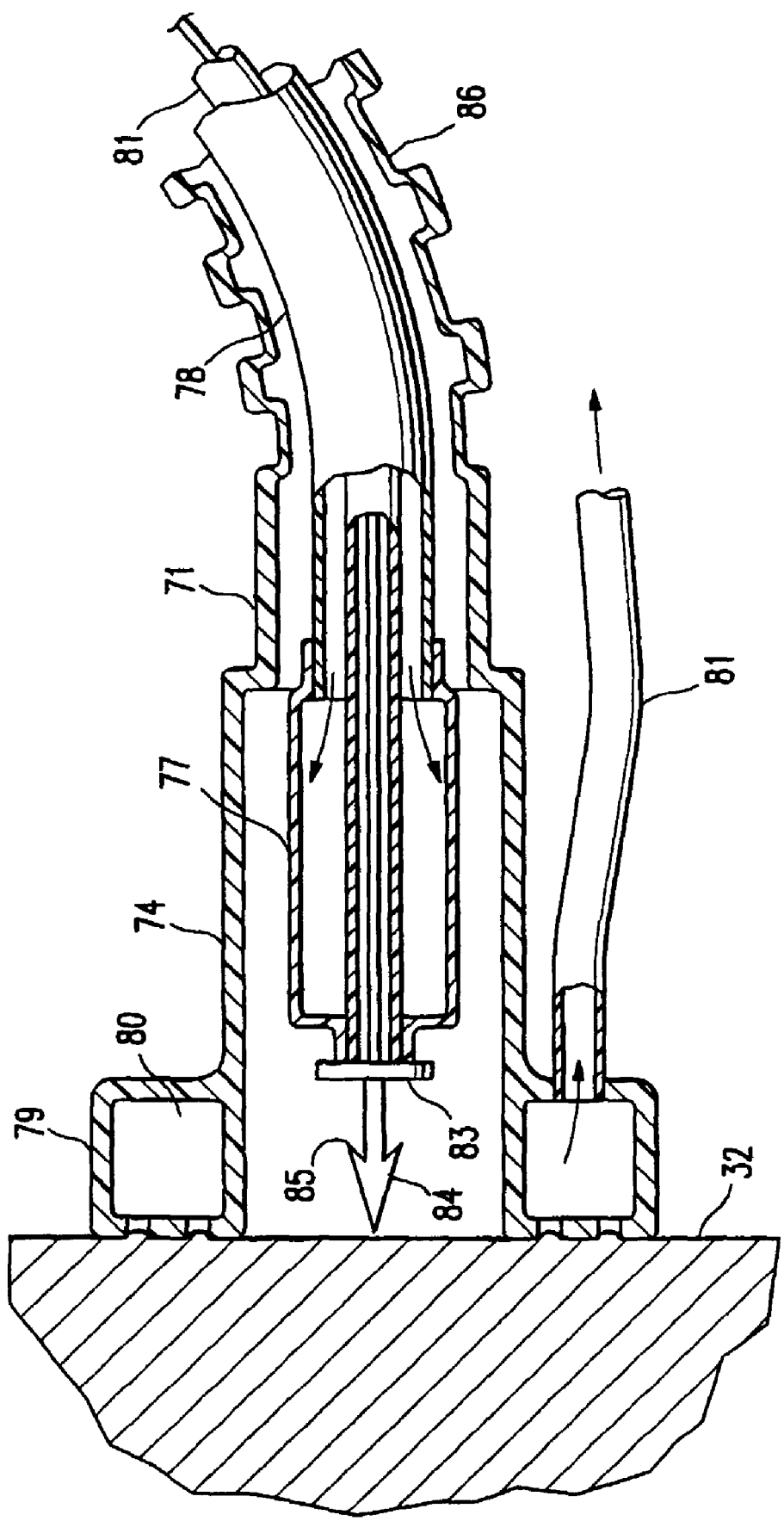
Figure 31:
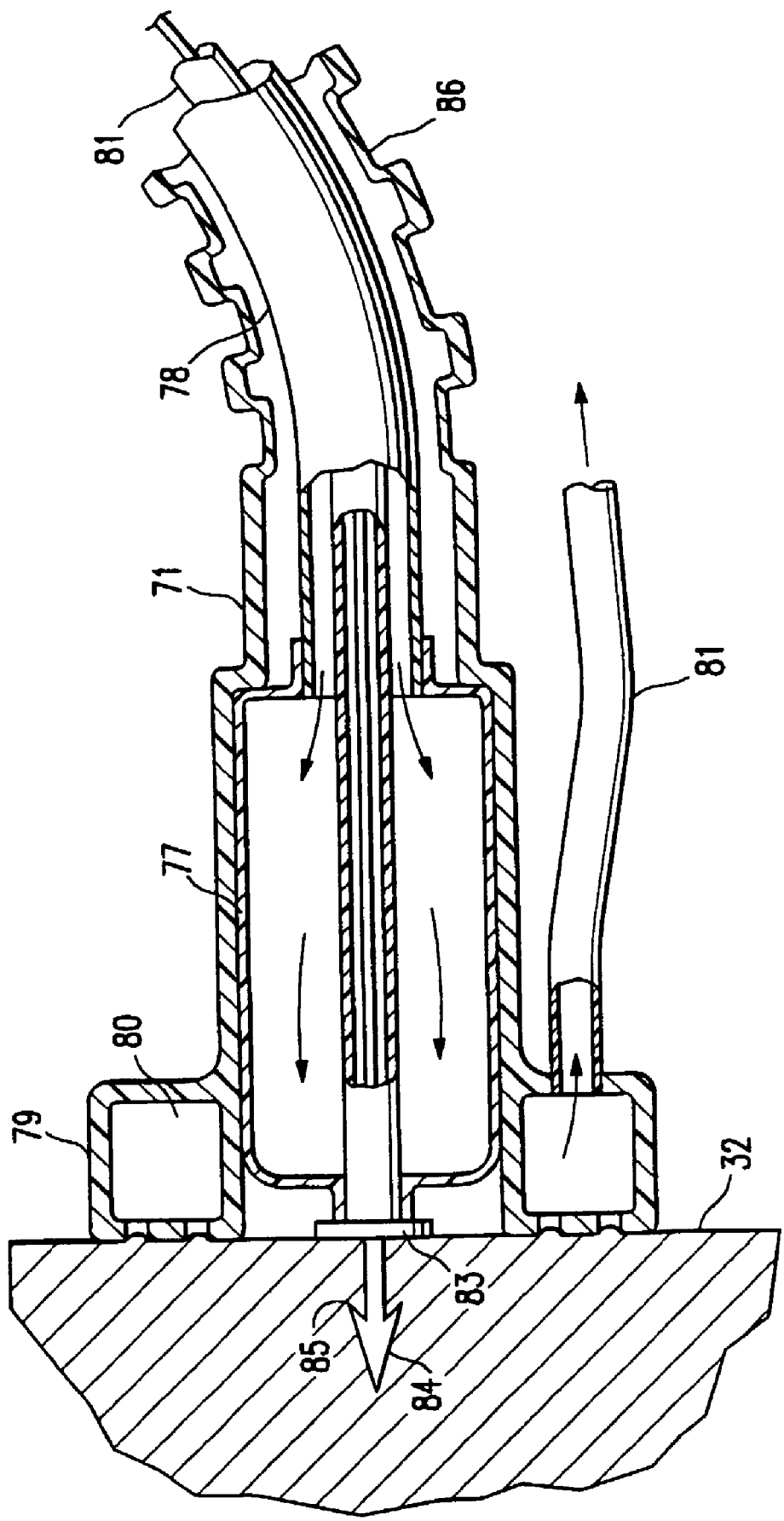

FIGS. 29-31 illustrate a suitable minimally invasive device for implanting a pacing lead in a patient's heart wall.

Figure 32:
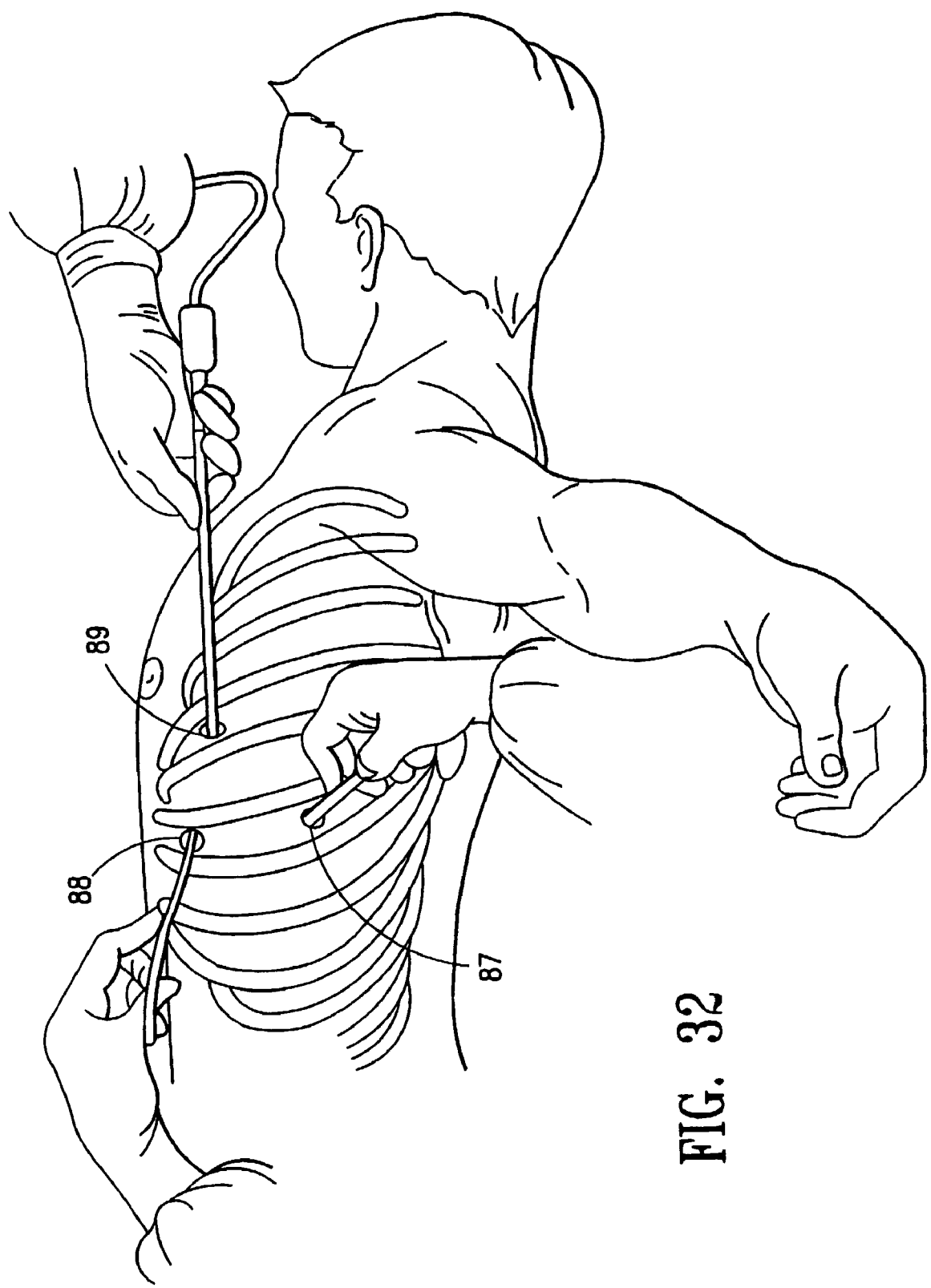

FIG. 32 illustrates typical locations for trocars in a patient's chest for performing procedures described herein.

FIGS. 33 and 34 illustrate an alternative embodiment of a minimally invasive device for implanting a pacing lead in a patient's heart wall.

FIG. 35 is a partial elevational view of an alternative penetrating electrode construction.

Figure 36:
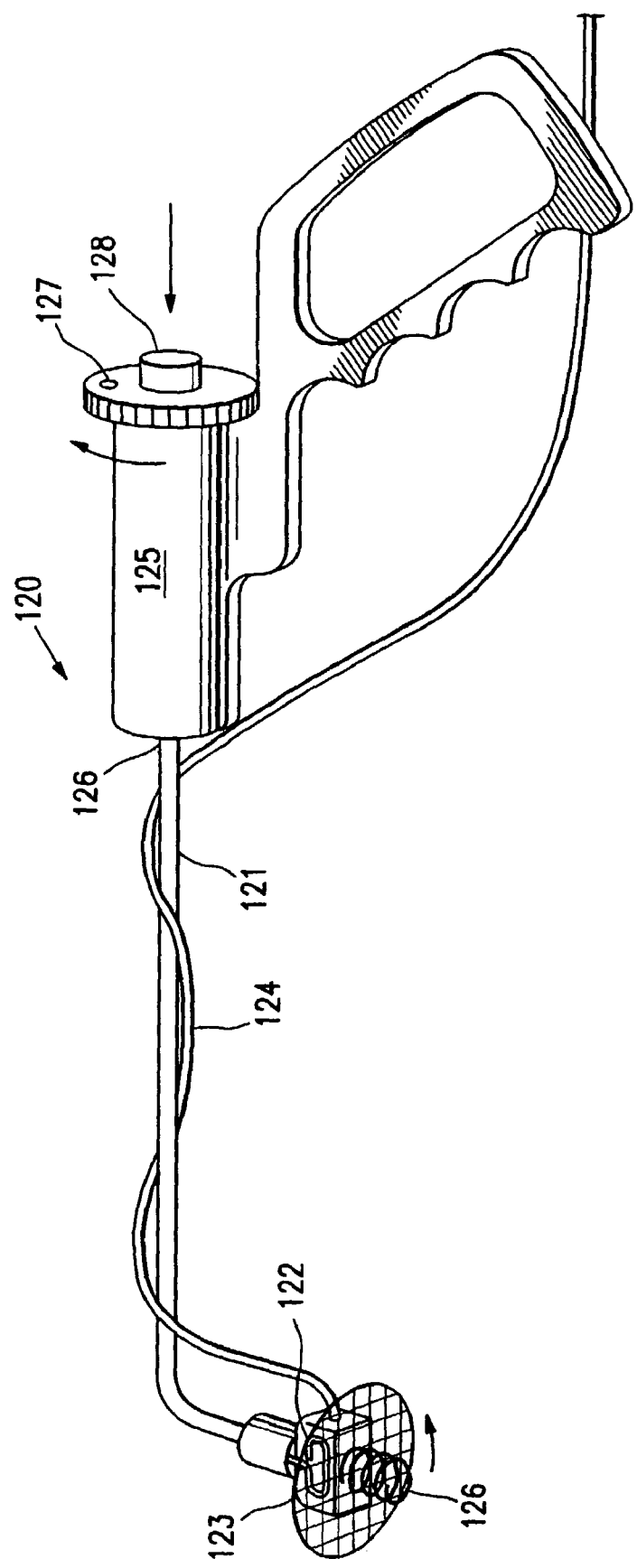

FIG. 36 illustrates another minimally invasive device for implanting a pacing lead in a patient's heart wall.

Figure 37:
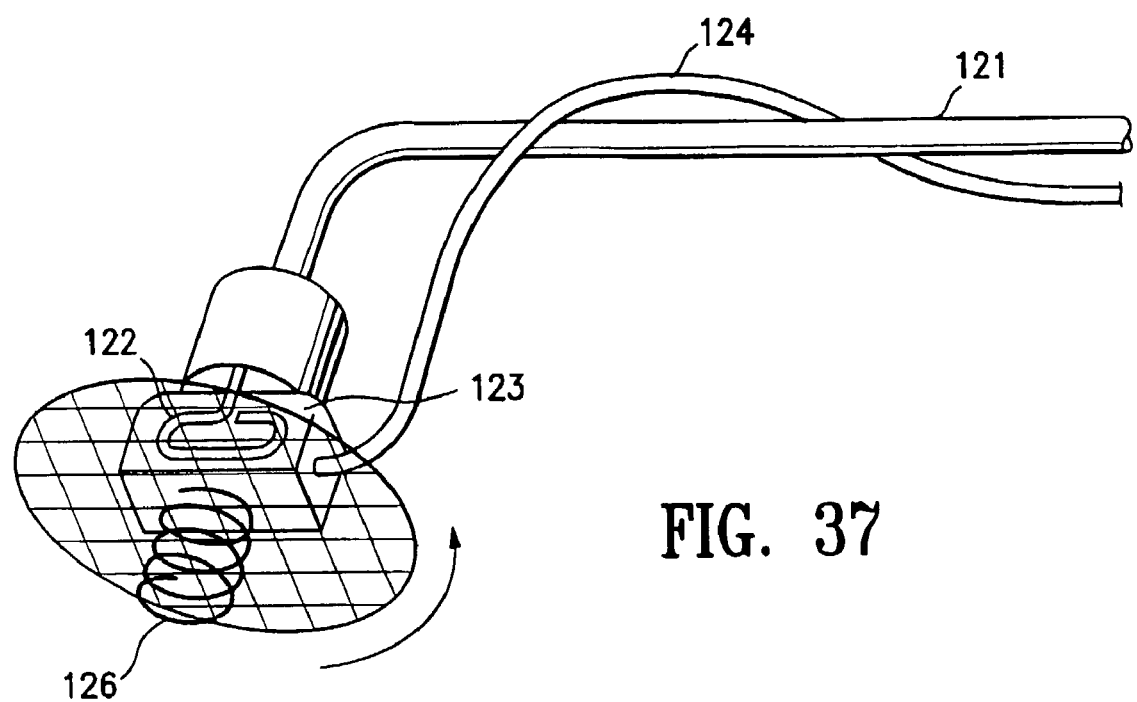
Figure 38:
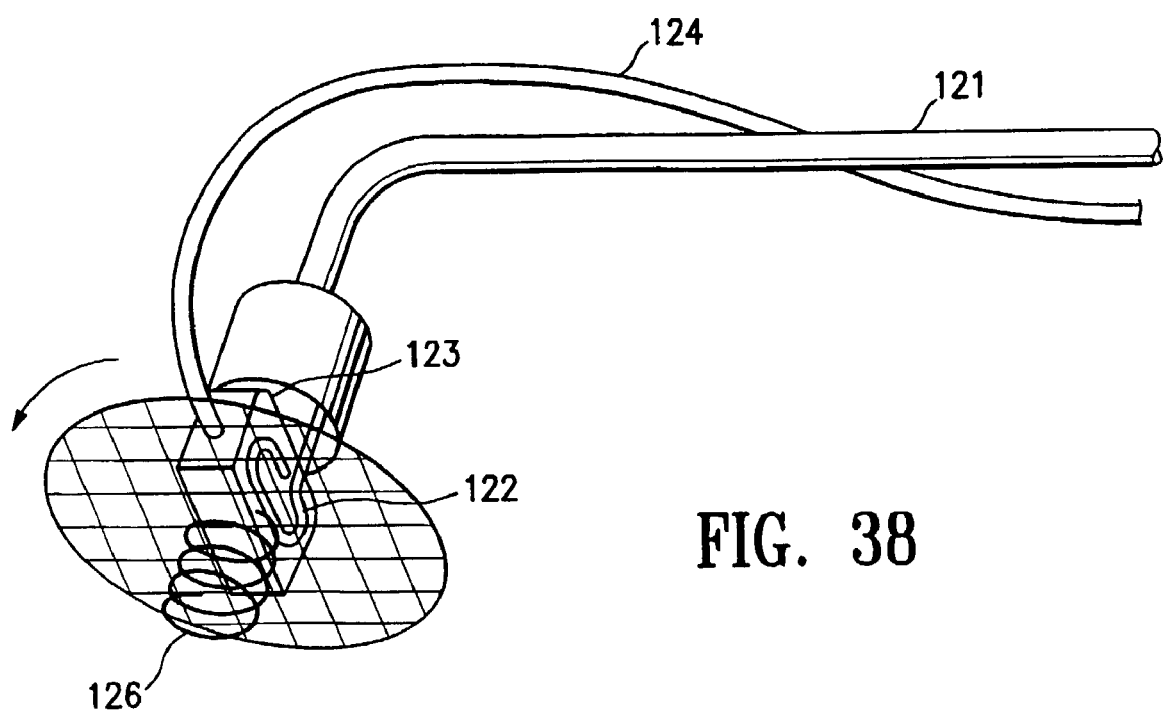

FIGS. 37 and 38 illustrate the grasping of the pacing lead by the minimally invasive device shown in FIG. 35 and the rotation thereof to implant the electrode in the ventricular wall of a patient.

The drawings are schematic presentations and not necessarily to scale.

DETAILED DESCRIPTION OF EMBODIMENTS OF THE INVENTION

Figure 1:
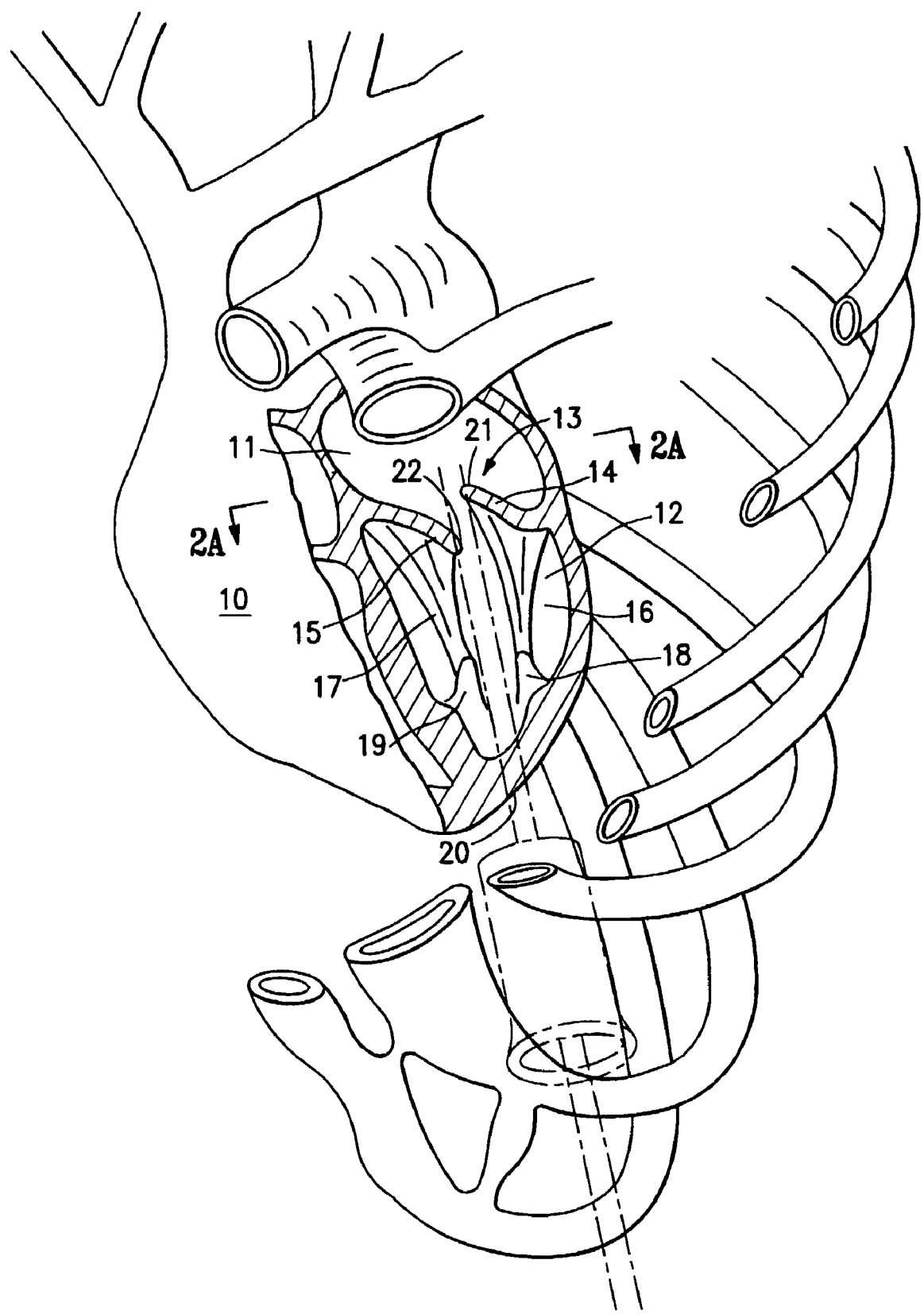
FIG. 1 is a perspective view of a patient's chest, partially illustrating the location of the patient's heart within the chest cavity, with part of the heart wall removed to expose the left ventricular chamber and to illustrate torn cordae tendenae connected to one of the valve leaflets.

FIG. 1 illustrates a patient's heart 10 with the left side of the heart in partial cross-section schematically showing the patient's left atrium 11 and left ventricle 12 with a mitral valve 13 disposed between the left atrium and the left ventricle having a posterior valve leaflet 14 and an anterior leaflet 15. Each of the valve leaflets 14 and 15 have cordae tendenae 16 and 17 respectively which are connected to the leaflets and to papillary muscles 18 and 19 respectively within the left ventricle at the apex 20 of the heart. The posterior leaflet 14 of the mitral valve 13 is shown with its cordae tendenae 16 partially torn. The free edge 21 of the posterior leaflet 14 is uncontrolled due to the torn cordae tendenae 16 which makes the valve incompetent to close completely when the heart contracts during systole. The incompletely closed mitral valve 13 results in regurgitation of blood back through the valve into the atrium 11 during systole which in turn results in lowered blood output for the left ventricle 12. The anterior valve leaflet 15 is shown with its cordae tendenae 17 completely attached.

Figure 2A:
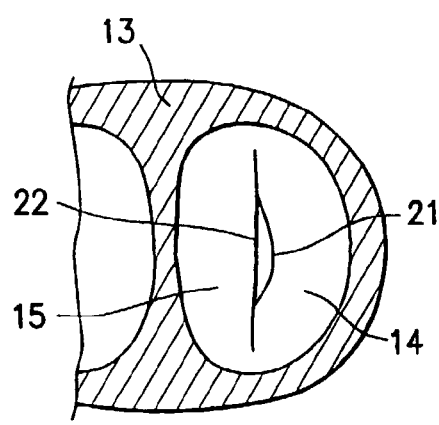
FIG. 2A is a transverse cross-sectional view taken along the lines 2A-2A shown in FIG. 1 illustrating the incompetent mitral valve in a closed condition during systole.
Figure 2B:
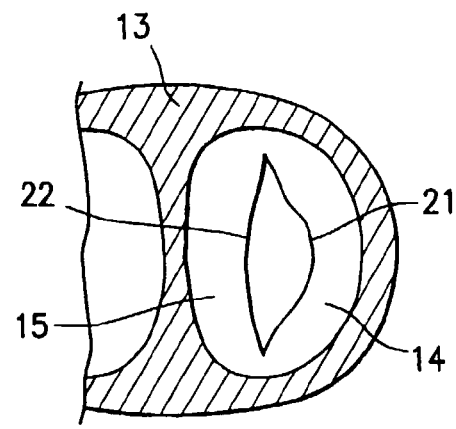
FIG. 2B is a transverse cross-sectional view taken along the lines 2A-2A shown in FIG. 1 illustrating the incompetent valve in an open condition during diastole.

FIGS. 2A and 2B illustrate the closed and open condition respectively of an incompetent mitral valve 13 such as that shown in FIG. 1. The free edge 21 of posterior valve leaflet 14 is unable to close completely against the free edge 22 of anterior leaflet 15 due to the torn cordae tendenae as depicted in FIG. 1. A similar leaflet condition may occur due to dilated ventricular architecture, i.e. dilated cardiomyopathy, which is also characteristic of congestive heart failure.

Figure 3A:
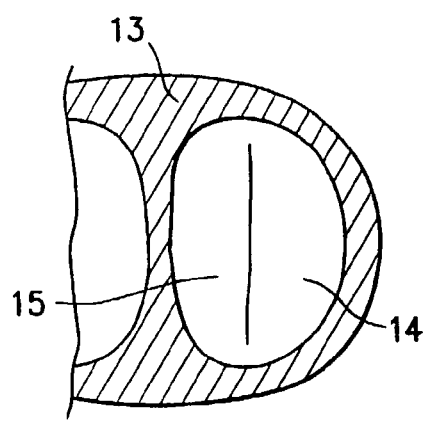
FIGS. 3A and 3B are transverse cross-sectional views similar to those shown in FIGS. 2A and 2B but illustrating a competent mitral valve.
Figure 3B:
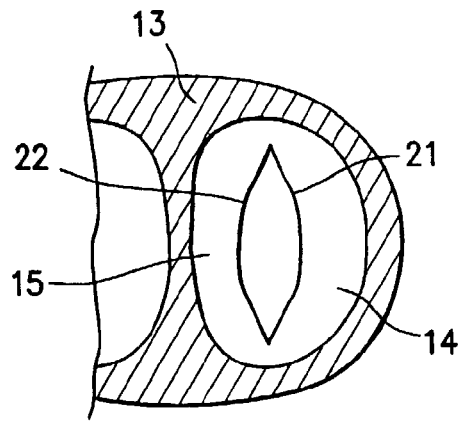

FIG. 3A illustrates a healthy competent mitral valve 13 with valve leaflets 14 and 15 which are closed completely during systole to prevent regurgitation of blood through the valve. FIG. 3B illustrates the competent mitral valve shown in FIG. 3A in an opened condition during diastole to allow blood to flow from the left atrium to the left ventricle.

Figure 4A:
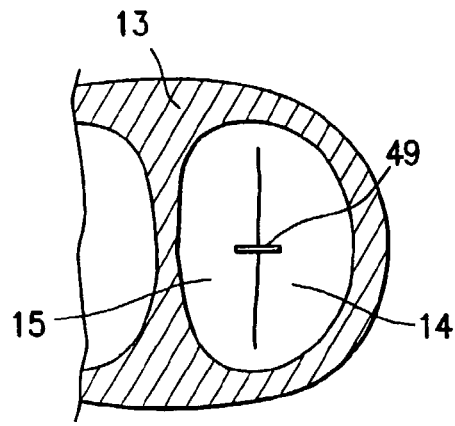
FIGS. 4A and 4B are transverse cross-sectional views similar to those shown in FIGS. 2A and 2B wherein the valve leaflets are secured together in a "Bow-Tie" configuration.
Figure 4B:
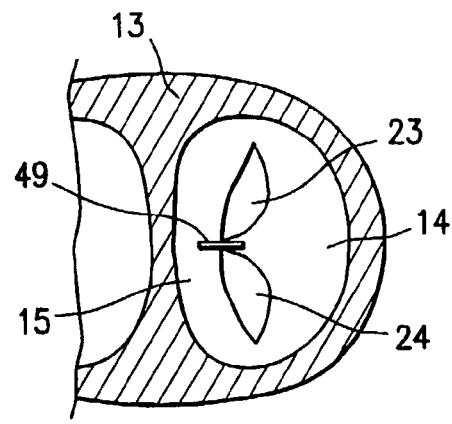

FIGS. 4A and 4B illustrate the closed and opened conditions of a mitral valve 13 in which the free edge 21 of posterior valve leaflet 14 and the free edge 22 of the anterior leaflet valve 15 are secured together in a "Bow-Tie" connection by a suitable clip, such as is shown in FIG. 26. During systole, when the heart contracts, the clip holds the free edges 21 and 22 of the valve leaflets together to minimize blood regurgitation through the valve. However, during diastole, when the heart muscle relaxes and the blood pressure within the left ventricle 12 is reduced, the mitral valve 13 opens up much like a competent valve but with two openings 23 and 24 between the valve leaflets 14 and 15. The interference with blood flow through the two openings 23 and 24 of a repaired mitral valve with a Bow-Tie connection between the leaflets is minimal during diastole compared to the flow with a single opening for a competent mitral valve.

Figure 5:
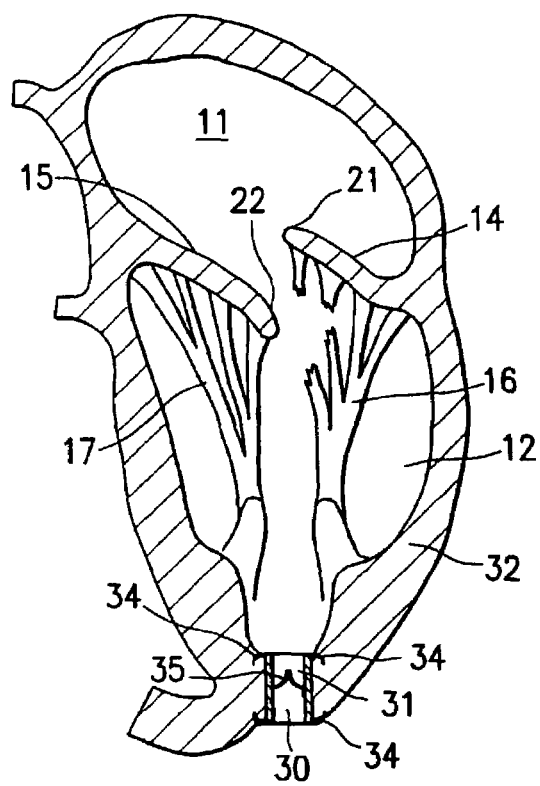
FIG. 5 is a partial elevational view in section of a patient's left ventricle and left atrium illustrating a ventricular wall valve seated in the apical ventricular wall.
Figure 7:
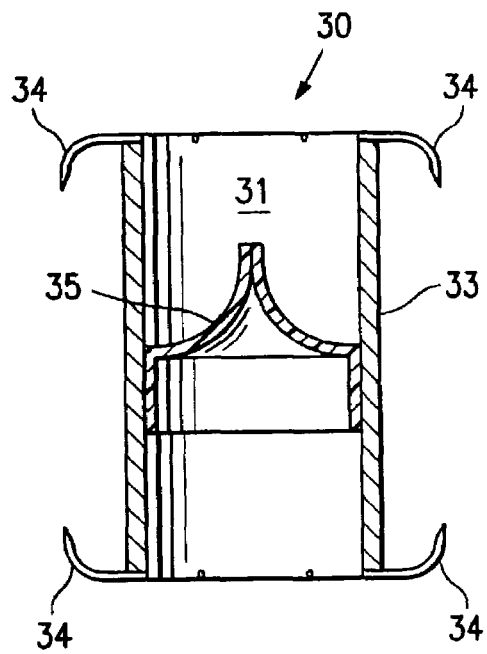
FIG. 7 is an enlarged elevational view in section taken along the lines 7-7 shown in FIG. 6.
Figure 6:
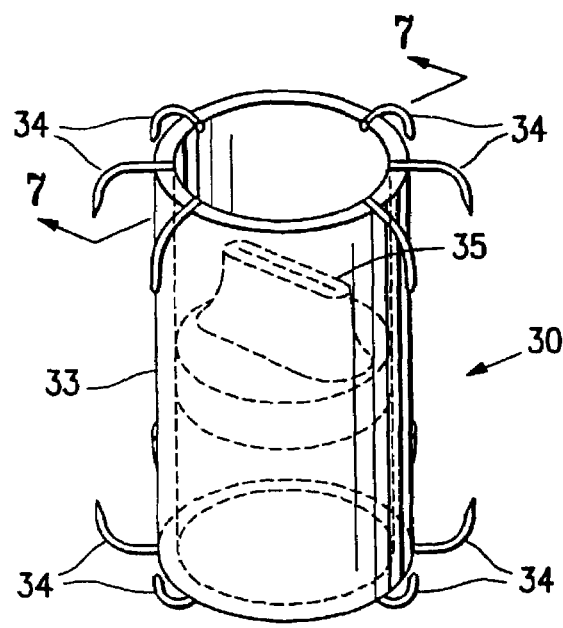
FIG. 6 is an enlarged perspective view of the ventricular wall valve shown in FIG. 5.
Figure 8:
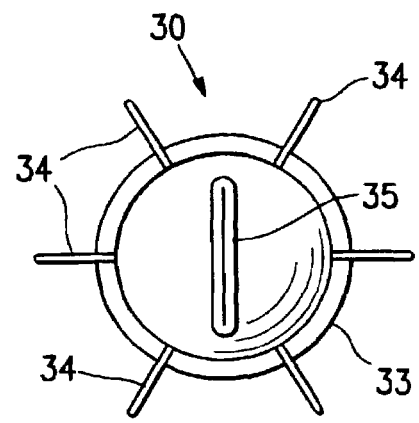
FIG. 8 is a top view of the valve taken along the line 7-7 shown in FIG. 6.
Figure 9:
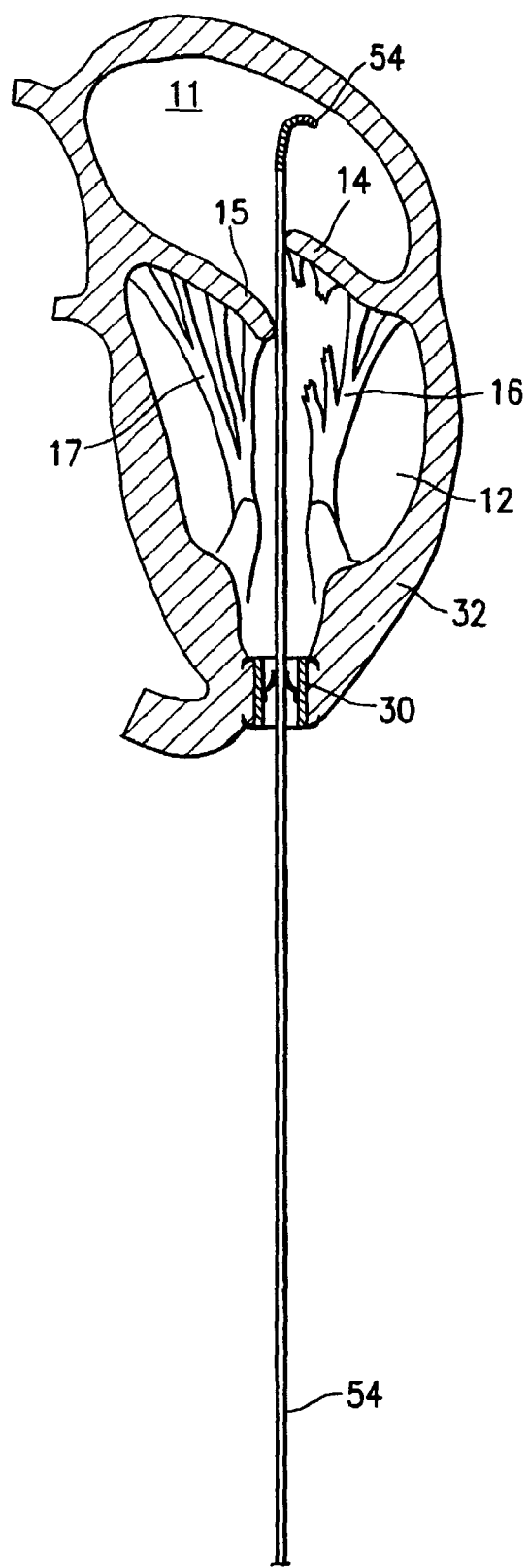
FIG. 9 is a partial elevational view, in section of the left side of the patient's heart illustrating the positioning of a guide wire in the patient's heart interior with the shaped distal tip of a guide wire in the patient's left atrium.

FIG. 5 illustrates a left side of a patient's heart such as is shown in FIG. 1 with an incompetent mitral valve 13 due to torn cordae tendenae 16. A valve 30 embodying features of the invention is deployed within a passageway 31 through the free ventricular heart wall 32. As is shown in more detail in FIGS. 6-8, the valve 30 has a cylindrical structure 33 which is secured within the passageway 31 by elements 34 which may be barbs or hooks. Other means such as suitable adhesives may be utilized to secure the valve 30 within the passageway 31. The valve component 35 of valve 30 is a duck billed valve component formed of suitable polymeric material which allow the passage of instruments for deployment or treatment but prevent or at least minimize loss of blood through the heart wall, particularly during systole. The duck-billed valve component 35 extends toward the distal end of the valve 30 to prevent blood flow from the heart chamber. The cylindrical structure 33 may be in an open-walled form similar to a stent and is preferably expandable to facilitate its deployment within the passageway 31. However, the cylindrical structure 33 may have any suitable structure or be formed of any suitable material which supports the valve component 35. The securing elements 34 may be forced into the surrounding tissue of the heart wall by means of a dumbbell shaped inflatable balloon (not shown).

Figure 17:
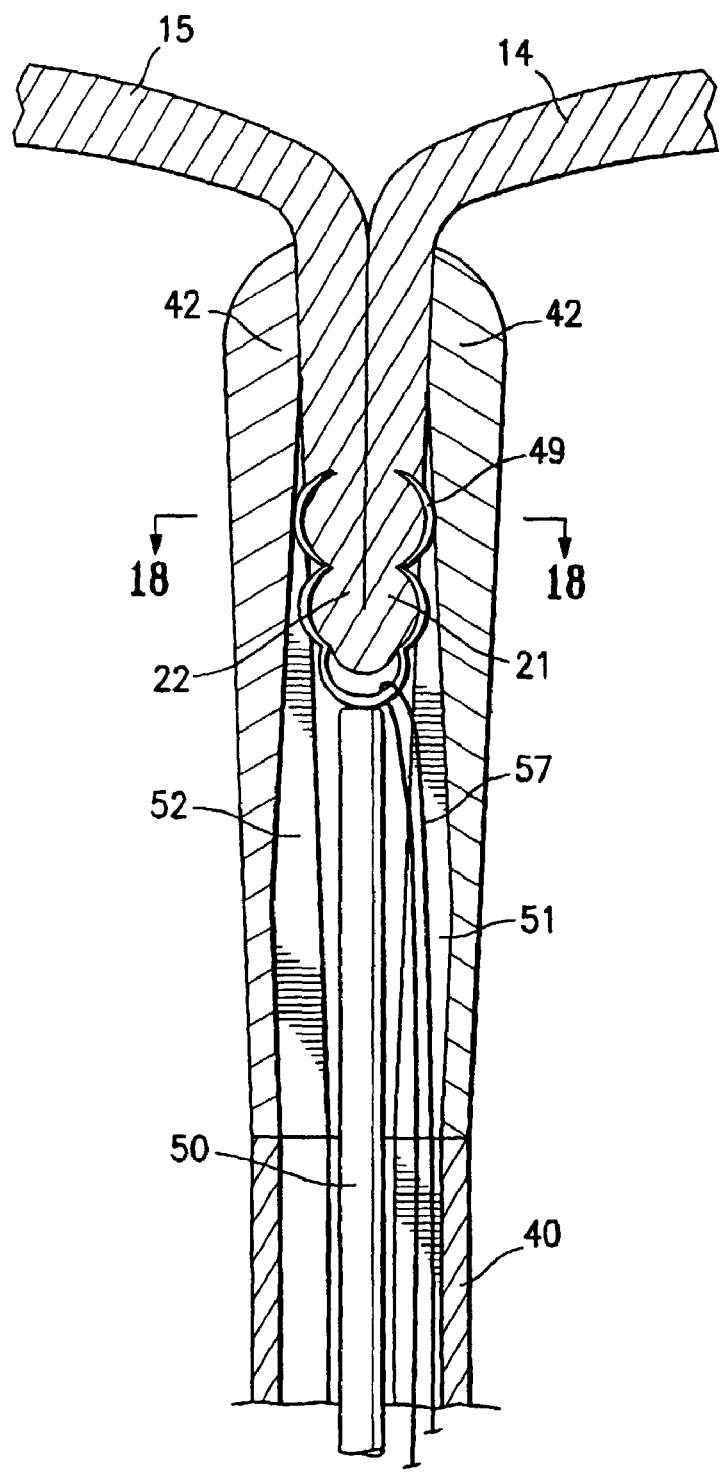
FIG. 17 is an enlarged view of the distal end of the grasping device as shown in FIG. 16 with a clip is position partially pressed into a connecting relationship with the free edges of the valve leaflets.
Figure 18:
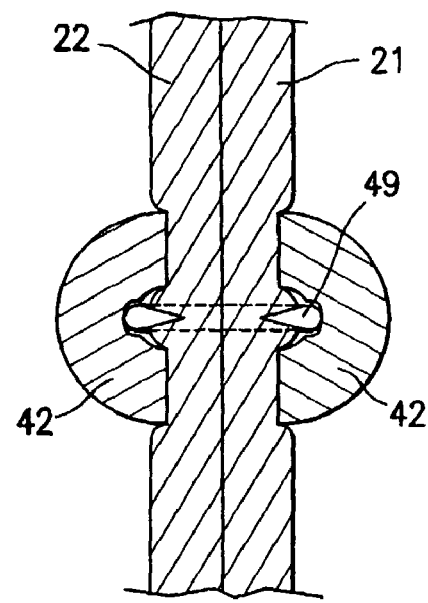
FIG. 18 is a transverse cross-sectional view taken along the lines 18-18 shown in FIG. 17 illustrating the clip partially connected to the valve leaflets.
Figure 21:
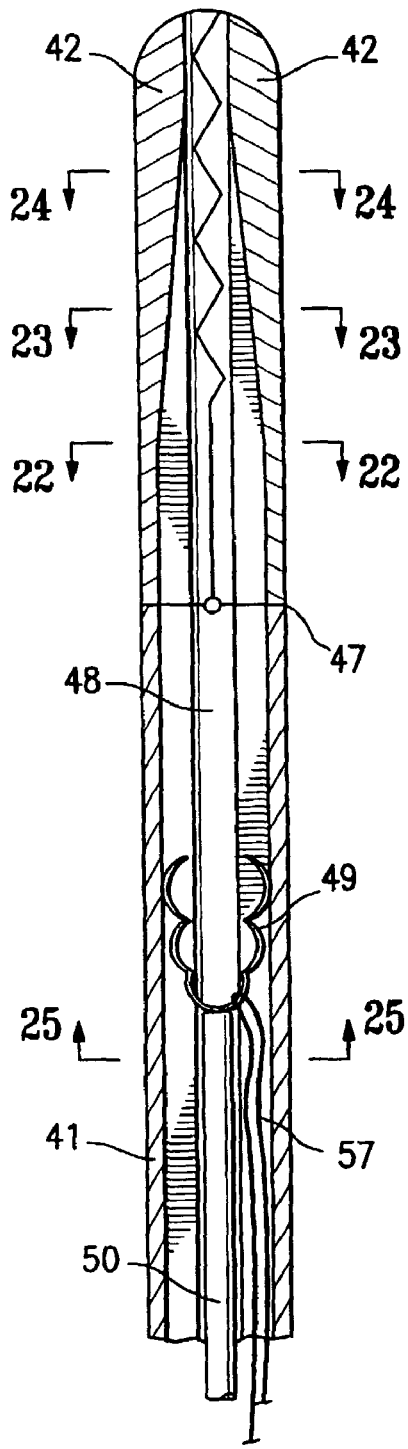
FIG. 21 is an enlarged longitudinal cross-sectional view of the distal end of the grasping device with a valve leaflet connecting clip slidably disposed within the inner lumen of the grasping device.
Figure 24:
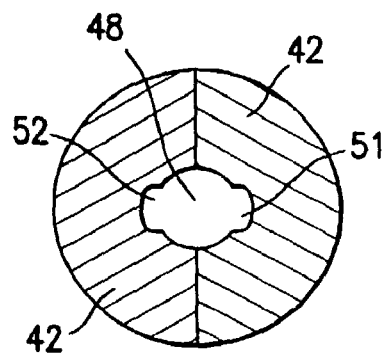
FIGS. 22-24 are transverse cross-sectional views taken along the lines 22-22, 23-23 and 24-24 respectively of the grasping device shown in FIG. 21.
Figure 23:
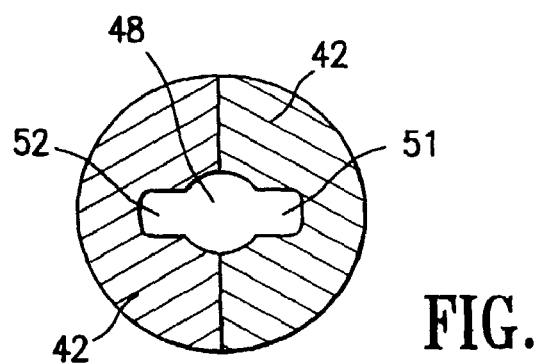
Figure 22:
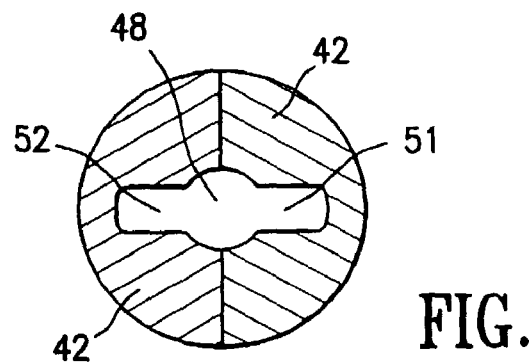
Figure 25:
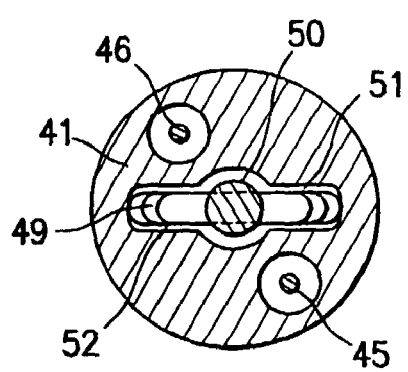
FIG. 25 is a transverse cross-sectional view taken along the lines 25-25 of the grasping device shown inn FIG. 21 illustrating the pusher bar pushing the leaflet connecting clip along the guide way lumen of the grasping device.

FIGS. 9-26 depict a grasping device 40 which embodies features of the invention and the use of the device to secure the valve leaflets in a Bow-Tie connection. The grasping device 40 has an elongated shaft 41, a plurality of grasping members or jaws 42 on the distal portion of the shaft and finger operated handles 43 and 44 which operate the jaws 42 through pull wires 45 and 46. The grasping members or jaws 42 are pivotally mounted at the pivot point 47 on the distal end of shaft 41. While only two jaws 42 are shown, three or more jaws may be employed. The elongated shaft 41 of grasping device 40 has an inner lumen 48 extending therein to allow for the passage of instruments that aid or effect the deployment of a connecting member 49 to the free edges of the valve leaflets to perform a Bow-Tie connection thereof as will be described in more detail hereinafter. FIG. 21 is an enlarged elevational view in section of the distal portion of the grasping device 40 to illustrate the connecting member 49, which is a leaflet clip, and the pusher bar 50 which pushes the clip through the inner lumen 48 of the grasping device. As shown in more detail in FIGS. 22-24, tapered grooves 51 and 52 are provided in the jaws 42 so that, as the clip 49 is pushed toward the distal ends of the jaws 42, the open distal ends of the clip slide along the tapering grooves and are closed against free edges 21 and 22 of the leaflets 14 and 15 grasped by the jaws. The deployed leaflet clip 49 partially closed against the free leaflet edges 21 and 22 in a Bow-Tie connection is shown in FIGS. 17 and 18. The inner lumen 48 continues through the jaws 42 to a port 51 to allow passage of other instruments such as the distal portion of the balloon catheter 53 which stabilizes and positions the valve leaflets 14 and 15 in the grasping location as shown in FIG. 14.

Figure 10:
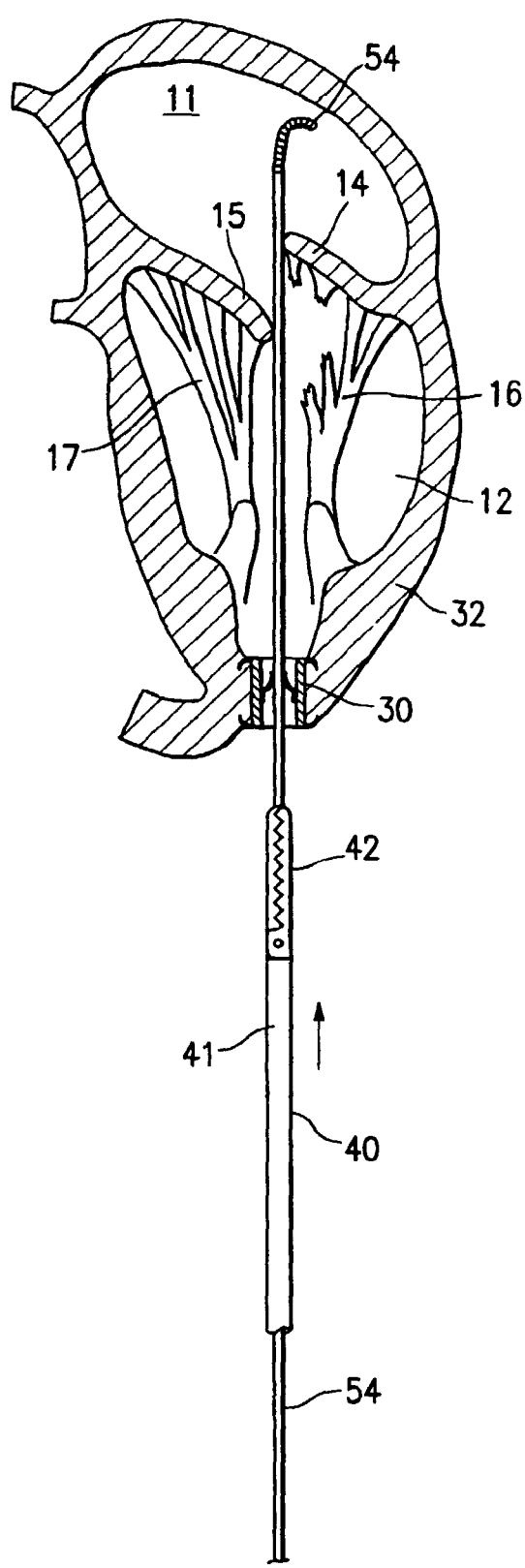
FIG. 10 is a partial elevational view, in section of the left side of the patient's heart illustrating the advancement of a grasping device over the guide wire shown in FIG. 9.
Figure 11:
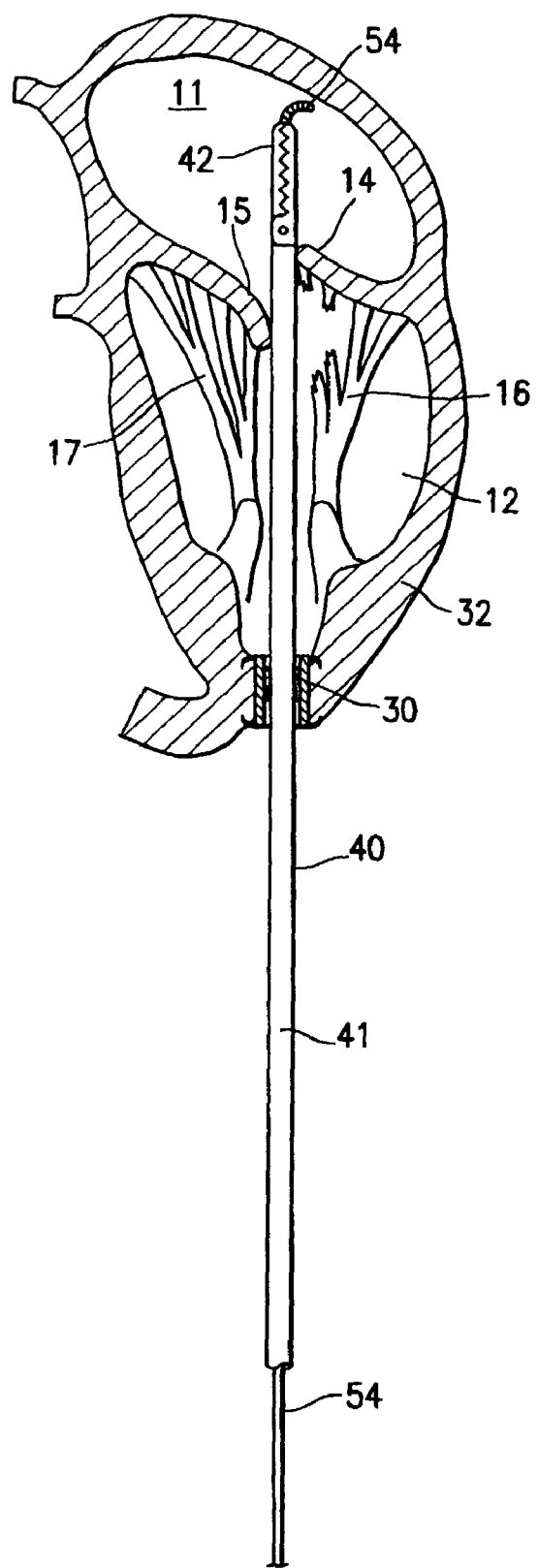
FIG. 11 is a partial elevational view, in section of the left side of the patient's heart illustrating the positioning of the grasping members on the distal end of the grasping device shown in FIG. 10 over the guide wire into the patient's left atrium.
Figure 12:
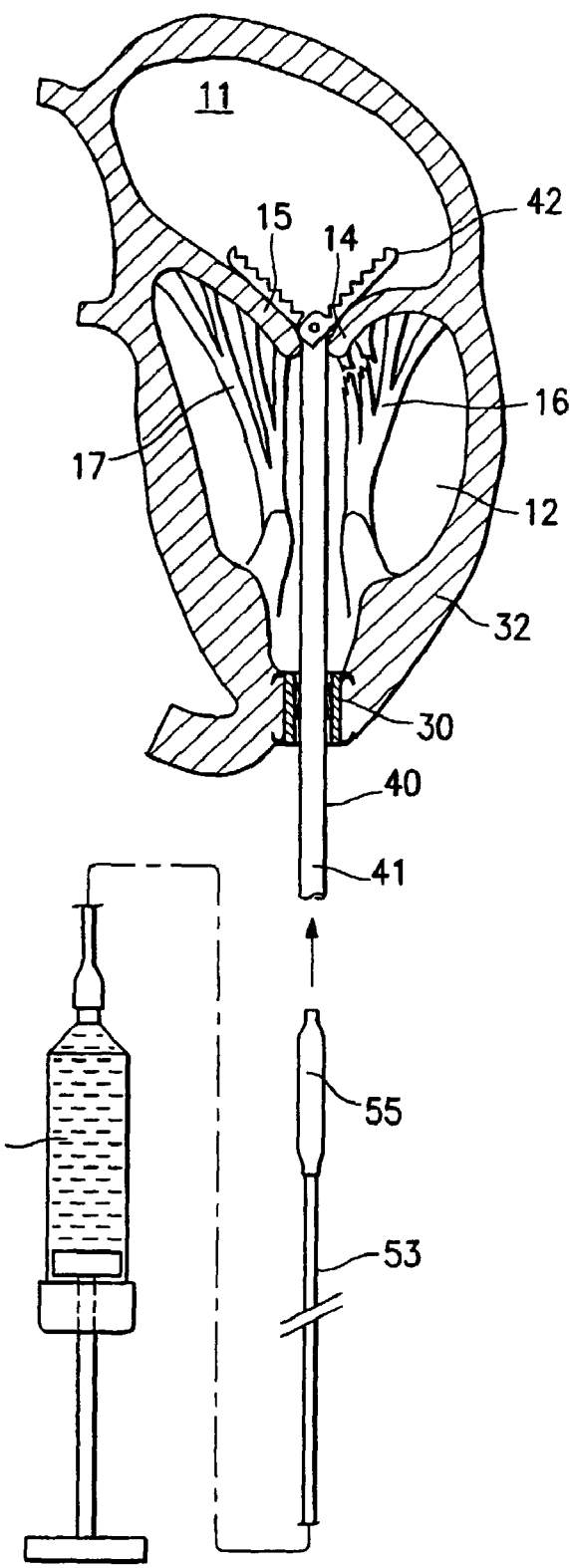
FIG. 12 is a partial elevational view, in section of the left side of the patient's heart illustrating the advancement of a balloon catheter into an inner lumen of the grasping device for deployment within the patient's left atrium.
Figure 13:
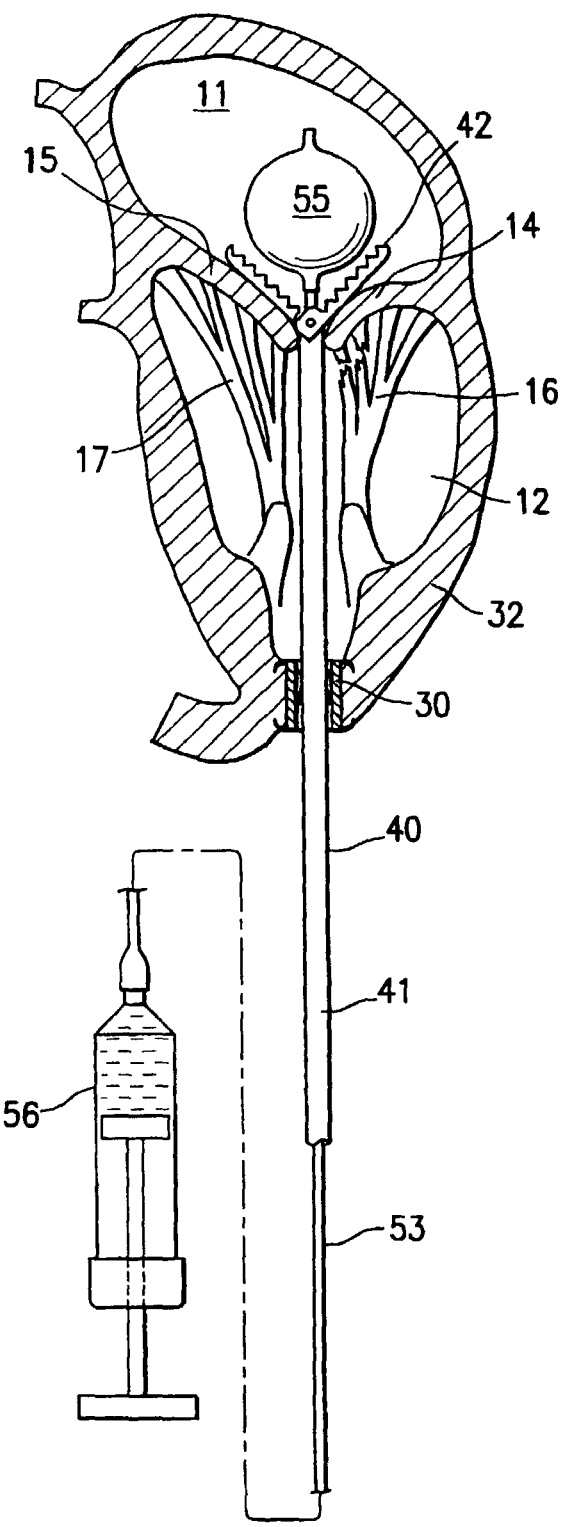
FIG. 13 is a partial elevational view, in section of the left side of a patient's heart illustrating the inflation of the balloon on the distal end of the balloon catheter within the patient's left atrium.

The use of the grasping device 40 to make a Bow-Tie connection of the free edges 21 and 22 of the mitral valve 13 is illustrated in FIGS. 9-18. After the one-way valve 30 is properly secured within the passageway 31 through the ventricular wall 32, a guide wire 54 is advanced through the valve 30 into the left ventricle 12 and further advanced through the mitral valve 13 into the left atrium 11 as shown in FIG. 10. A grasping device 40 is mounted on the proximal end of the guide wire 54 which extends out of the patient and is slidably advanced over the guide wire through the valve 30, and into the left atrium through the mitral valve 13. The guide wire 54 at that point is slidably disposed within the inner lumen 48 of the grasping device 40. A balloon catheter 53 may then be advanced over the guide wire 54 through the inner lumen 48 of the grasping device 40 until the inflatable balloon 55 on the distal portion of catheter 53 is disposed in the left atrium 11. The balloon 55 is inflated by injecting inflation fluid through an inner lumen (not shown) in the shaft of the balloon catheter 53 by means of the syringe 56 as shown in FIG. 13. If the shaft of the balloon catheter 53 is stiff enough, the guide wire 54 may be withdrawn prior to insertion of the balloon catheter 53 and the advancement thereof through the inner lumen 48 of grasping device 40 by itself.

Figure 14:
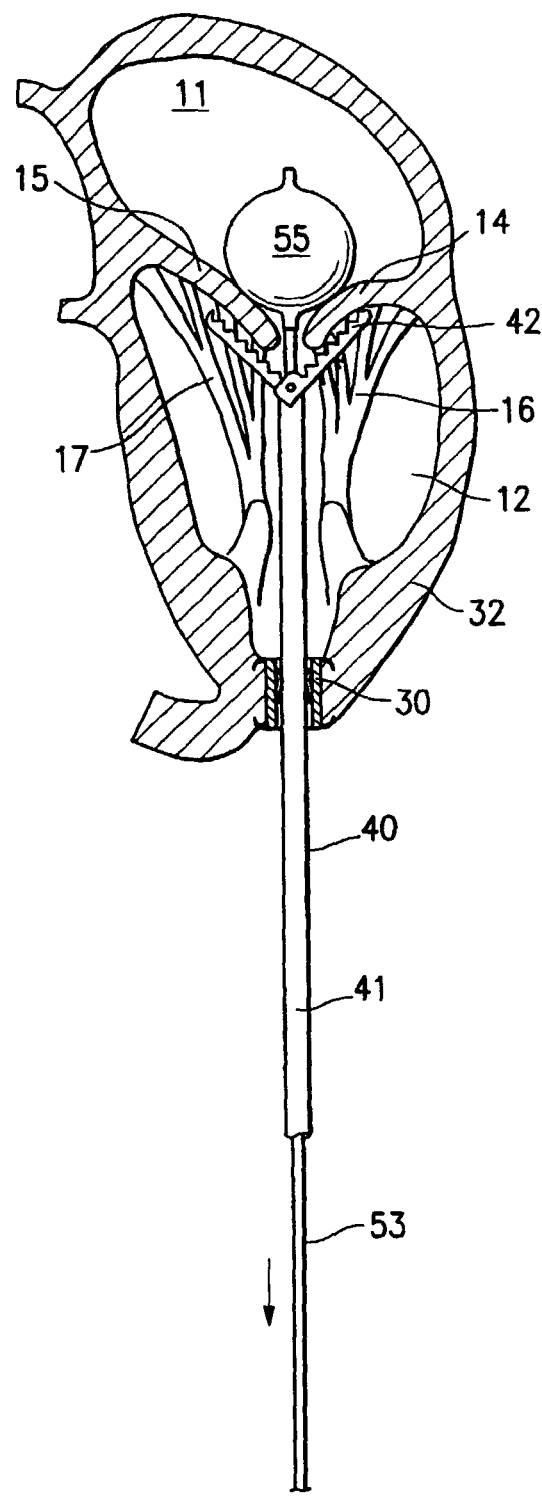
FIG. 14 is a partial elevational view, in section of the left side of a patient's heart illustrating the positioning of the valve leaflets in a grasping location by the balloon catheter with the open grasping members of the grasping device being disposed within the left ventricle in a position to grasp the valve leaflets.
Figure 15:
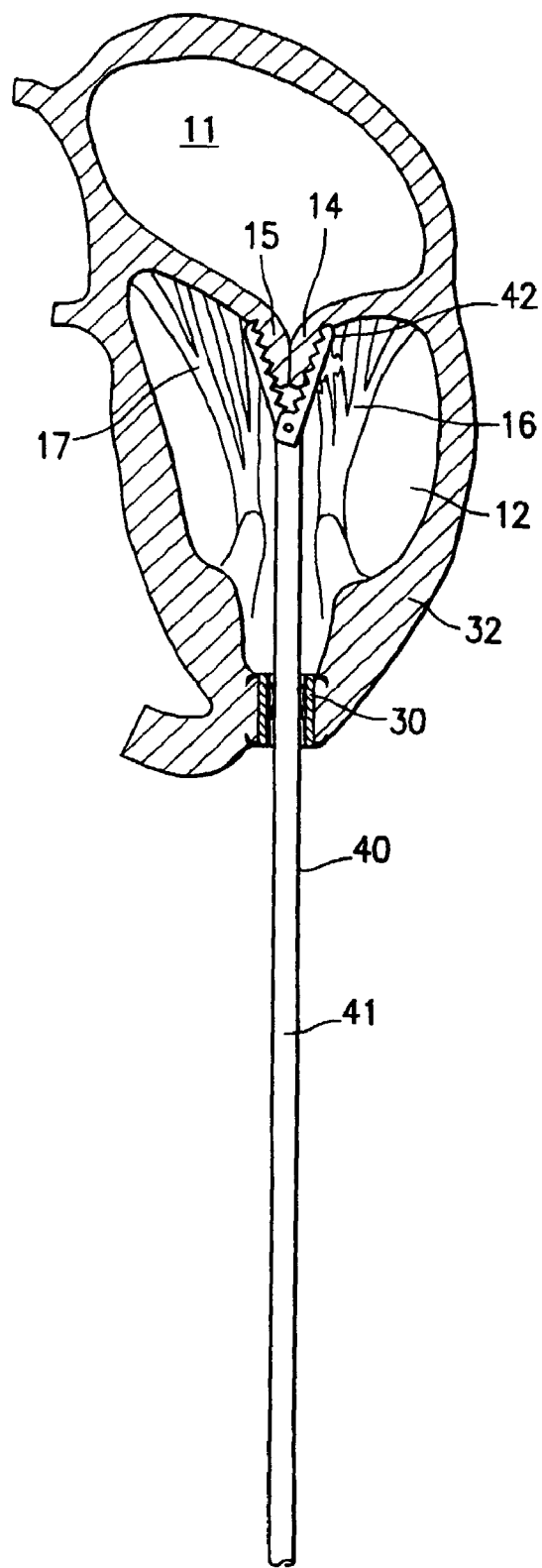
FIG. 15 is a partial elevational view, in section of the left side of a patient's heart illustrating the grasping of the valve leaflets by the grasping members of the grasping device.
Figure 16:
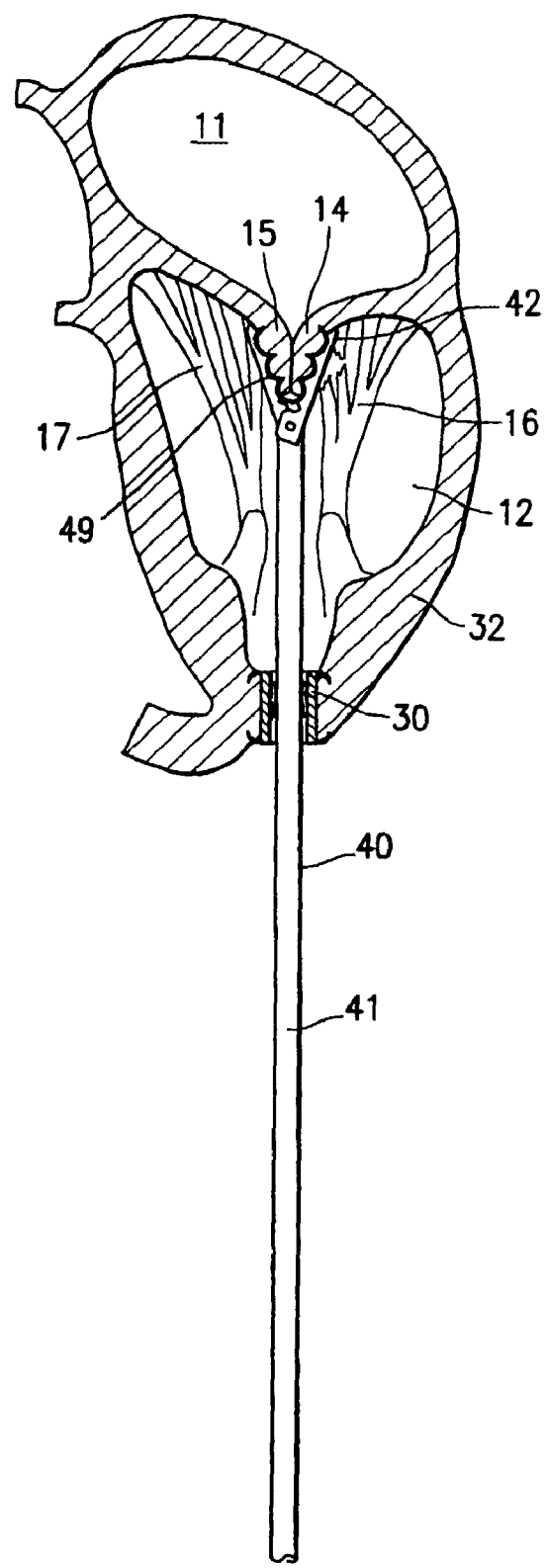
FIG. 16 is a partial elevational view, in section of the left side of a patient's heart illustrating the connecting the free edges of the valve leaflets with a clip in a Bow-Tie arrangement.

After the balloon 55 is inflated within the left atrium 11, the balloon catheter 53 is pulled proximally to press the inflated balloon 55 against the atrial side of the mitral valve leaflets 14 and 15 to urge the leaflets into grasping location as shown in FIG. 14. The jaws 42 of the grasping device 40 may then be closed on the valve leaflets 14 and 15 as shown in FIG. 15. As previously described, the leaflet clip 49 may then be advanced through the inner lumen 48 by pusher bar 50 to close the open ends of clip 49 against and through the grasped free edges 21 and 22 of valve leaflets 14 and 15 respectively, as shown in FIGS. 17 and 18. After the clip 49 has been deployed to form the Bow-Tie connection, the grasping device 40 and any other devices that may be present are withdrawn from the patient's heart through the ventricular wall valve 30. The duck-billed valve component 35 closes down after removal of the various instruments and prevents loss of blood from the left ventricle. If desired, the valve 30 may be left in place or it may be removed and the proximal opening of the ventricular passageway sutured or otherwise closed or sealed.

In FIG. 26A a clip 49 is shown with a strand 57 secured to the closed proximal end. An alternate embodiment is depicted in FIG. 26B in which the closed proximal end of the clip 49 is provided with an eyelet 58. One end of the strand 57 is tied to the eyelet. A variety of clip structures may be employed to connect the free edge of the valve leaflets.

An embodiment is shown in FIG. 27 wherein an elongated strand 57 formed of relatively non-compliant material, such as PTFE, Nylon, polyethylene terephthalate, has its distal end secured to the closed proximal end of leaflet clip 49. The strand 57, if formed of PTFE, should have a transverse dimension of about 1 to about 3 mm. After deployment of the clip 49 to connect the free edges 21 and 22 of the leaflets 14 and 15 in a Bow-Tie connection, the proximal end of the strand 57 is pulled taut to position the leaflets 14 and 15 in a position to ensure proper closure during systole and then the proximal end of the strand 57 is secured to the free ventricular wall 32, preferably to the exterior thereof, such as shown suturing with a pledget 59 while maintaining the strand in a taut condition. This embodiment is particularly suitable in those instances wherein cordae tendenae connected to the valve leaflet are torn. The strand 57 acts as an artificial cordae tendenae to the leaflet. However, care must be exercised when securing the proximal end of the strand 57 is secured to the heart wall 32 so that the valve leaflets are in a natural position in order to prevent or reduce regurgitation through the mitral valve 13.

The hearts of many CHF patients exhibit intraventricular conduction delay with resulting disturbance of the synchronous right and/or left ventricular contractility. As previously mentioned, a large population of the CHF patients are not suitable candidates for or fail percutaneous delivery of pacing leads to provide relief from CHF. In these instances, it has been found that a pacing lead secured to the exterior wall defining in part the heart chamber exhibiting the conductance delay can better control the contraction of the heart and thereby improve the chamber's ejection.

As shown in FIG. 28, the pacing lead 60 can be deployed within the patient's chest cavity by minimally invasive techniques through a trocar 61 located in the intercostal space between the patient's ribs. The placement of the pacing lead 60 can be observed by an endoscopic video 62 extending through a second trocar (not shown) in a second intercostal space. Instruments to facilitate the implantation of the helically shaped penetrating electrode 63 of the pacing lead 60 can be passed through the trocar 61 and the electrode secured within the heart wall 32 by minimally invasive techniques. The pacing lead 60 has its proximal end configured to be electrically connected to a pacing power source 64 which is preferably disposed at a subcutaneous location. The pulsed output of the power source 64 may be controlled in a conventional manner to provide the desired contractions to the heart wall to which the pacing lead is secured.

FIGS. 29 to 31 illustrate a minimally invasive embodiment having features of the invention directed to implanting a pacing lead in a patient's heart wall. The delivery and implanting device 70 of this embodiment includes a tubular delivery member 71 having a proximal end 72 with a port 73, an enlarged distal end 74 with a port 75 and inner lumen 76 extending within the tubular member from the proximal port 73 to the distal port 75. The distal end 74 of the tubular member 71 is enlarged to receive a longitudinally expansive member such as inflatable balloon 77. The balloon 77 is provided with an elongated shaft 78 having an inner inflation lumen (not shown) which allows inflation fluid to be introduced into the interior of the balloon to inflate the balloon. The distal end 74 of tubular member 71 is provided with a securing pod or ring 79 to releasably secure the distal end to the exposed surface of the free ventricular wall 32. The interior chamber 80 of the pod 79 is connected in fluid communication with the vacuum tube 81 which is in turn configured to be connected in fluid communication with a vacuum source (not shown). The pacing lead 82 has a collar 83 secured about a distal portion thereof which is configured to be engage by the balloon 77 when the latter is inflated. The enlarged end 74 of the tubular delivery member 71 prevents complete radial expansion of the balloon 77 upon inflation and as a result the balloon expands longitudinally. The longitudinal expansion of balloon 77 against the collar 83 connected to the pacing lead 82 drives the penetrating electrode 84 on the pacing lead against the exposed ventricular wall 32 so that the penetrating electrode 84 penetrates into and is secured within the ventricular wall 32 by the barbs 85. The enlarged distal end 74 should be about 5 to about 15 mm in diameter and about 5 to about 40 mm in length. Other sizes may be suitable. The tubular member 71 may have a flexible section 86 to facilitate articulation of the distal extremity of the tubular member 71 to aid in the placement of the pod 79 to the exterior of the heart wall 32 and provide a sound seal for the application of a vacuum. The vacuum pod 79 is configured to pass through a trocar provided in an intercostal space between the patient's ribs.

The pacing lead 82 shown in FIGS. 29-32 is installed by first making a small opening in the patient's chest and deploying a first trocar 87 such as shown in FIG. 32 having an inner lumen within the small opening. Commercially available trocars include trocars from U.S Surgical and others. A second similar trocar 88 to place a variety of instruments within the patient's chest cavity for the procedure and a third trocar 89 is installed in a similar manner for a thoracoscope which allows the operating surgeon to view the region in which the pacing lead is to be installed. Other trocars may also be installed for other purposes. A suitable arrangement of trocars 87, 88, 89 for such procedures is shown in FIG. 32.

To install the pacing lead the lower left lobe of the patient's lung, which is deflated, is moved out of the way to expose the patient's heart. Part of the pericardium on the free wall 32 defining in part the patient's left ventricle is removed to expose a desired region of the epicardial site in which the pacing lead 81 is to be secured. The pacing lead delivery tube 71 is introduced into the patient's chest cavity through the first trocar and advanced within the chest cavity toward the exposed epicardial surface. The distal end facing of the vacuum pod 79 on the expanded distal end 74 of the delivery tube 71 is pressed against the exposed epicardial surface of the ventricular wall 32 and a vacuum is developed within the inner chamber 80 of the pod 79 to hold the distal end of the tubular member 71 against the epicardial surface as shown in FIG. 30. Inflation fluid is introduced into the interior of the balloon 77 through the inflation lumen in tube 78 as shown by the arrows. The expanded distal end 74 of the delivery tube 71 limits the radial expansion of the balloon 77, so that the balloon expands longitudinally in the distal direction as shown in FIG. 31. The longitudinal expansion causes the distal end of the balloon to expand against the collar 83 secured to the distal portion of the pacing lead 81.

Balloon pressure on the collar 83 drives the pacing lead 82 toward the epicardial location and this results in the penetration of electrode 84 on the distal end of the pacing lead into the ventricular wall 32. The barbs 85 on the penetrating electrode 84 secure the electrode within the heart wall and resist withdrawal of the electrode from the heart wall 32. Electrical pulses from a suitable electrical power source are applied to the proximal end of the pacer lead. The electrical pulses are transmitted through the pacing lead conductor to the penetrating electrode 83 secured within the heart wall 32. The pulses are emitted from the secured electrode 84 into the tissue of the heart wall 32 to pace the patient's left ventricle. The pacing is controlled in order to increase the volume of blood pumped out of the heart chamber.

An alternative device 90 is shown in FIGS. 33 and 34 which has an elongated tubular shaft 91 with a proximal end 92, a distal end 93, and a semispherical shaped housing 94 on the distal end with a securing pod 95 on the distal end 93. The securing pod 95 has an annular vacuum chamber 96 around the lower edge of the semi-spherical housing 94 which is in fluid communication with the inner lumen 97 of tubular member 98. The proximal end (not shown) of the tubular member 98 is configured to be connected in fluid communication with a vacuum source (not shown). An inner lumen 99 extends through the tubular shaft 91 and slidably receives the catheter 100 having an inflatable balloon 101 on the distal end thereof. A pacing lead 102 extends along, but exterior to, the tubular shaft 91 and has a distal end with a balloon support platform 103 and a tissue penetrating electrode 104 extending away from the platform.

A distal portion 105 of the tubular shaft 91 is provided with some degree of flexibility in order to ensure that the spherical housing 94 is in a proper orientation to be pressed against and releasably secured to the exposed epicardial surface. With the securing pod 95 secured against the epicardial surface of wall 32, the balloon 101 is inflated to drive the supporting platform 103 and the connected penetrating electrode 104 toward the epicardial surface. The electrode 104 is driven into the wall 32 of the patient's left ventricle and the barbs 106 thereon secure the electrode within the wall tissue to resist withdrawal of the electrode from its deployed position. Electrical pulses from a suitable power source may then be applied to the tissue within the heart wall to pace the contraction thereof as discussed above to increase the output of blood from the heart chamber.

The balloon 101 is releasably secured to the support platform 103 so that when the electrode 104 is driven into the heart wall 32, the balloon 101 can be deflated and the vacuum within the vacuum chamber of the semispherical housing may be released and the assembly withdrawn from the patient through the trocar through which it was delivered. The proximal end of the pacing lead may then be directed to the power source and connected thereto. The shaft 91 is preferably shapeable in order to be able to place the pacing lead at the desired location on the exposed epicardial surface. The shaft 91 may be formed of stainless steel, or other metallic or other materials which allow the shaft to be manually shaped by the physician prior to insertion into the patient's chest cavity.

The tissue penetrating electrodes 83 and 104 described in the aforesaid embodiments generally have an arrow shape with a pointed distal tip to facilitate tissue penetration and two outwardly flaring barbs 85 and 106 which resist electrode withdrawal once the electrode is in place. Alternate electrode construction includes a fish-hook shaped electrode such as shown in FIG. 34 with a pointed distal tip and a single outwardly flaring barb. Similar electrode constructions are suitable including those having three or more outwardly flaring barbs.

Another alternative embodiment is shown in FIGS. 35-37, which is a device 120 having an elongated tube 121 with a pair of grasping tongs 122 on the distal end 123 of the tube with a mechanism (not shown) configured to secure the tongs 121 to a pacing lead housing 124. The device 120 of this embodiment has a housing 125 on the proximal end 126 with a rotating lead holder 127 which when rotated rotates the pair of grasping tongs 122 as shown in FIGS. 37 and 38. A release button 128 is provided on the housing 125 to disengage the grasping tongs 122 from the pacing lead housing 124. The rotation of the tongs 122 causes the rotation of the pacing lead housing 124 and the helical electrode 126 to screw into the heart wall 32. A similar device will soon be offered by Medtronic as an epicardial lead implant tool (Model No. 10626) which is designed to be used with a Model 5071 pacing lead.

Usually, an additional (e.g., conventional) pacing lead is installed in the patient's right ventricle for complete resynchronization of the heart chambers. The additional lead is preferably connected to the same power source as the first described pacing lead which may be located in the infraclavicular pocket in a conventional manner.

EXAMPLE

Twenty patients were selected (12 men, 8 women) for thorocoscopically direct left ventricular lead placement. The patients had New York Heart Association Class III or IV congestive heart failure with a mean ejection fraction of 20%±8%. All of the patients had previously undergone transvenous right-ventricular lead placement and subcutaneous implantation of a dual or triple chamber pacemaker but had failed transvenous left-ventricular lead placement due to suboptimal coronary vein anatomy. Surgical entry into the left chest was carried out through a 2 cm incision in the mid acillary line at the sixth intercostal space, following collapse of the left lung. A 15 mm thoracoport (trocar 87 in FIG. 32) from U.S. Surgical was inserted with the tip of the trocar pointing to the left minimize contact with the heart. A 5 mm rigid port (trocar 88 in FIG. 32) was inserted inferolateral to the left nipple of the patient in the sixth intercostal space to allow insertion of a grasper such as the U.S. Surgical Endograsper. Another 5 mm rigid port (trocar 89 in FIG. 32) was inserted in the fourth intercostal space at the anterior axillary line for a scope and camera. A portion of the pericardium was removed to provide an exposed epicardial region by a grasper from within trocar 88 for implantation of the helical electrode of the pacing lead. Screw in epicardiac leads (Medtronic 5071 and Guidant 4047) were inserted through the 15 mm trocar or rigid port under video control by a scope within the trocar 89. The leads were inserted into the epicardium by applying gentle pressure and three clockwise full rotations of the pacing lead holder (shown schematically in FIGS. 34-36). If pacing voltage thresholds were unacceptably high the pacing lead would be twisted one-quarter turn and then retested. Acceptable pacing lead placement is defined as 100% pacing at 2.5 volts or less. The video assisted left-ventricular lead placement was successful in nineteen of the twenty patients. The one failure required an open thorocotomy.

While particular forms of the invention have been illustrated and described, it will be apparent that various modifications can be made without departing from the spirit and scope of the invention. For example, the vacuum actuated securing pod to secure the distal end of a delivery tube may be replace in whole or part by one or more hooks or tissue gasping components disposed about the distal end of the delivery device to releasably secure the distal end to the epicardial surface during electrode placement. To the extent not otherwise described, the various components of the devices described herein may be formed of conventional materials and have conventional structures. Accordingly, it is not intended that the invention be limited to the specific embodiments illustrated. It is therefore intended that this invention to be defined by the scope of the appended claims as broadly as the prior art will permit. Moreover, those skilled in the art will recognize that features shown in one embodiment may be utilized in other embodiments. Terms such as "element", "member", "device", "section", "portion", "component", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety.

What is claimed is:

1. A minimally invasive method of treating a patient's heart, comprising:
   a. accessing an exterior region of the patient's heart wall which defines in part the left ventricle;
   b. providing a pacing lead which has an attached housing with opposed grasping surfaces and which has a tissue penetrating electrode extending distally from the housing in electrical conducting relationship with the pacing lead;
   c. advancing the pacing lead through a small opening in the patient's chest cavity to the accessed region of the patient's heart wall;
   d. providing a pair of rotatable tongs configured to grasp and rotate the pacing lead housing;
   e. grasping the opposed grasping surfaces of the housing with the pair of rotatable tongs;
   f. securing the pacing lead to the accessed region of the patient's heart wall by pressing the penetrating electrode of the pacing lead against the accessed exterior region of the patient's heart wall with the tongs and rotating the grasped pacing lead housing with the tongs while pressing the penetrating electrode against the accessed region to drive the penetrating electrode into the heart wall so as to remain therein when the tongs are released; and
   g. delivering electrical pulses through the pacing lead to the penetrating electrode of the pacing lead within the heart wall to control the contraction of the heart wall to which the pacing lead is secured.

2. The method of claim 1 wherein a trocar is disposed in the small opening in the patient's chest to gain access to the patient's chest cavity.

3. The method of claim 1 wherein the electrical pulses have a frequency, duration, current and voltage sufficient to control the contraction of the patient's left ventricle to increase the output thereof.

4. The method of claim 1 wherein a second pacing lead is disposed in the right ventricle of the patient's heart and electrical pulses are emitted from an electrode on a distal portion of the second pacing lead having a frequency, duration, current and voltage sufficient to control the contraction of the right ventricle to increase the output thereof.

5. The method of claim 1 wherein an elongated delivery tube is provided which has a proximal end, a distal end configured to pass through the small opening in the patient's chest and an inner lumen extending to the distal end and configured to slidably receive the pacing lead when the pacing lead is advanced to the exposed region of the patient's heart wall.

6. The method of claim 5 wherein the delivery tube has a securing pod on the distal end thereof to releasably secure the distal end of the delivery tube to the exposed region of the patient's heart wall.

7. The method of claim 6 wherein the securing pod has a vacuum chamber and at least one vacuum conduit extending between the vacuum chamber and the leading surface of the securing pod and the securing pod is secured against the exposed region of the patient's heart wall by vacuum from within the chamber.

8. The method of claim 6 wherein the tongs are secured to a driving member associated with the delivery tube which is configured to close the tongs to engage the pacing lead housing and to rotate the housing in order to drive the penetrating electrode of the pacing lead into the exposed region of the patient's heart wall to secure the penetrating electrode within the heart wall.

9. The method of claim 8 wherein the driving member is an inflatable balloon which is disposed within the expanded distal end of the delivery tube.

* * * * *